US 8,885,032 B2

(12) United States Patent
Igarashi et al.

(10) Patent No.: US 8,885,032 B2
(45) Date of Patent: Nov. 11, 2014

(54) ENDOSCOPE APPARATUS BASED ON PLURAL LUMINANCE AND WAVELENGTH

(71) Applicant: Olympus Medical Systems Corp., Tokyo (JP)

(72) Inventors: Makoto Igarashi, Hachioji (JP); Kenji Yamazaki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 36 days.

(21) Appl. No.: 13/856,785

(22) Filed: Apr. 4, 2013

(65) Prior Publication Data

US 2013/0265401 A1    Oct. 10, 2013

Related U.S. Application Data

(63) Continuation of application No. PCT/JP2012/078744, filed on Nov. 6, 2012.

(30) Foreign Application Priority Data

Mar. 30, 2012  (JP) ................................. 2012-082287

(51) Int. Cl.
   *H04N 5/06*       (2006.01)
   *A61B 1/00*       (2006.01)
   *A61B 1/06*       (2006.01)

(52) U.S. Cl.
   CPC ............. *A61B 1/0661* (2013.01); *A61B 1/0638* (2013.01); *A61B 1/00009* (2013.01)
   USPC ........................................................ 348/68

(58) Field of Classification Search
   USPC ........................................................ 348/68
   See application file for complete search history.

(56) References Cited

U.S. PATENT DOCUMENTS

| 5,078,150 A | 1/1992 | Hara et al. | |
| 2005/0046702 A1* | 3/2005 | Katayama et al. | 348/222.1 |
| 2005/0206785 A1* | 9/2005 | Swan et al. | 348/448 |
| 2006/0018378 A1* | 1/2006 | Piccinelli et al. | 375/240.03 |
| 2007/0149854 A1 | 6/2007 | Igarashi | |
| 2007/0153542 A1 | 7/2007 | Gono et al. | |
| 2009/0091614 A1* | 4/2009 | Gono et al. | 348/68 |
| 2011/0069162 A1* | 3/2011 | Ozawa et al. | 348/68 |

FOREIGN PATENT DOCUMENTS

| EP | 1 787 577 A1 | 5/2007 |
| JP | 02-104332 | 4/1990 |
| JP | 2006-061621 | 3/2006 |
| JP | 2006-141711 | 6/2006 |

(Continued)

*Primary Examiner* — Y Lee
*Assistant Examiner* — Salame Amr
(74) *Attorney, Agent, or Firm* — Scully, Scott, Murphy & Presser, P.C.

(57) ABSTRACT

An endoscope apparatus includes a light source apparatus, and a light-adjusting circuit. The light-adjusting circuit, based on a first image signal with a first wavelength band having a peak wavelength of a spectral characteristic and a second image signal with a second wavelength band having a peak wavelength of a spectral characteristic providing a value lower than that of the first image signal in the absorption characteristic and providing a suppressed scattering characteristic of the body tissue between a wavelength band providing a maximal value and a wavelength band for a minimal value in an absorption characteristic of a body tissue of a subject, provides a weight larger than that of the second image signal to the first image signal to calculate a light adjustment signal for adjusting a light amount in a light source apparatus and outputs the light adjustment signal.

15 Claims, 14 Drawing Sheets

(56) References Cited

FOREIGN PATENT DOCUMENTS

| JP | 2006-239205 A | 9/2006 |
| JP | 2010-075368 | 4/2010 |
| JP | 2011-050470 | 3/2011 |
| JP | 2011-143154 | 7/2011 |
| WO | WO 2006/025334 A1 | 3/2006 |

* cited by examiner

ENDOSCOPE APPARATUS BASED ON PLURAL LUMINANCE AND WAVELENGTH

CROSS REFERENCE TO RELATED APPLICATION

This application is a continuation application of PCT/JP2012/078744 filed on Nov. 6, 2012 and claims benefit of Japanese Application No. 2012-082287 filed in Japan on Mar. 30, 2012, the entire contents of which are incorporated herein by this reference.

BACKGROUND OF THE INVENTION

1. Field of the Invention

The present invention relates to an endoscope apparatus and specifically relates to an endoscope apparatus that can display a blood vessel in an inner portion of a subject.

2. Description of the Related Art

Conventionally, in a medical field, various less-invasive examinations and surgical operations using endoscopes have been performed. A surgeon can insert an endoscope into a body cavity to observe an image of an object picked up by an image pickup apparatus provided in a distal end portion of an insertion portion of the endoscope and as necessary, perform a treatment of a lesion site using a treatment instrument inserted through the inside of a treatment instrument channel. The surgical operations using endoscopes eliminate the need for, e.g., laparotomy, and thus, provide the advantage of reducing a physical burden on patients.

An endoscope apparatus includes an endoscope, an image processing apparatus connected to the endoscope, and an observation monitor. An image of a lesion site is picked up by an image pickup device provided in a distal end portion of an insertion portion of the endoscope, and the image is displayed on the monitor. A surgeon can perform diagnosis or a necessary treatment while viewing the image displayed on the monitor.

Also, examples of the endoscope apparatuses include those that enable not only normal light observation using white light, but also special-light observation using special light such as infrared light in order to observe blood vessels in inner portions.

In the case of infrared endoscope apparatuses, for example, indocyanine green (ICG) having the characteristic of having an absorption peak in a region of near-infrared light with wavelengths of around 805 nm is injected into the blood of a patient as a medical agent. Then, infrared light with wavelengths of around 805 nm and infrared light with wavelengths of around 930 nm are irradiated to an object in a time division manner from a light source apparatus. A signal of an image of the object picked up by a CCD is inputted to a processor in the infrared endoscope apparatus. For example, as disclosed in Japanese Patent Application Laid-Open Publication No. 2000-41942, as such infrared endoscope apparatuses, those in which a processor assigns an image with wavelengths of around 805 nm to a green signal (G) and an image with wavelengths of around 930 nm to a blue signal (B) and outputs the signals to a monitor are proposed. Since an image of infrared light with image of around 805 nm, which is well absorbed by ICG, is assigned to green, a surgeon can observe an infrared image with good contrast when ICG administration is performed.

For example, in an endoscopic submucosal dissection (ESD) in which a submucosal layer in which a lesion site exists is dissected and removed using an endoscope, in order to prevent relatively thick blood vessels in a mucous membrane from being cut by, e.g., an electrosurgical knife, a surgeon performs a treatment such as dissection after confirming the positions of such blood vessels. Blood vessels that may cause heavy bleeding run from a submucosal layer to an intrinsic muscle layer.

SUMMARY OF THE INVENTION

An endoscope apparatus according to an aspect of the present invention includes: an illumination section that irradiates at least one illuminating light having a predetermined wavelength band to a subject; an image pickup section that picks up an image of return light from the subject based on the irradiation by the illumination section; an image signal processing section that generates an image signal based on an image pickup signal from the image pickup section; a light-adjusting section that, based on a first luminance value based on a signal with a first wavelength band that is a narrow band and a second luminance value based on a signal with a second wavelength band that is a narrow band between a wavelength band providing a maximal value and a wavelength band providing a minimal value in a light absorption characteristic of hemoglobin in a body tissue of the subject in a red band in a visible range, the signal with the second wavelength band providing an absorption coefficient lower than that of the signal of the first wavelength band in the light absorption characteristic of hemoglobin and providing a suppressed scattering characteristic of the body tissue, performs processing for addition of the first luminance value provided with a weight coefficient larger than that of the second luminance value and the second luminance value to calculate a light adjustment signal for adjusting a light amount in the illumination section and outputs the light adjustment signal; and an illumination control section that controls an amount of light irradiated by the illumination section based on the light adjustment signal outputted from the light-adjusting section.

DETAILED DESCRIPTION OF THE PREFERRED EMBODIMENTS

Embodiments of the present invention will be described below with reference to the drawings.

First Embodiment (Configuration of Endoscope Apparatus)

An embodiment of the present invention will be described below with reference to the drawings.

Figure 1:
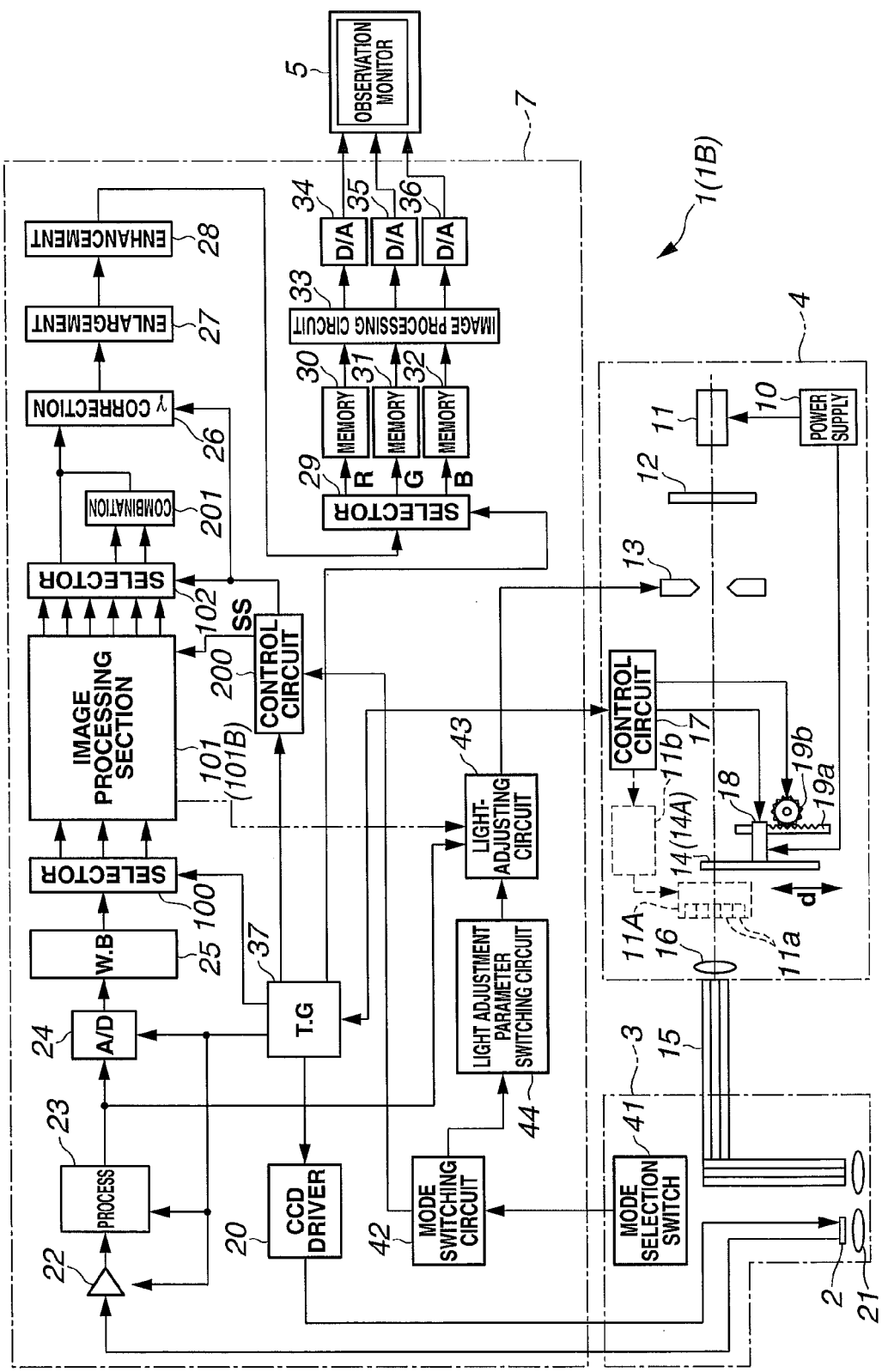
FIG. 1 is a configuration diagram illustrating a configuration of an endoscope apparatus according to a first embodiment of the present invention.

First, a configuration of an endoscope apparatus according to the present embodiment will be described. FIG. 1 is a configuration diagram illustrating a configuration of an endoscope apparatus according to the present embodiment.

As illustrated in FIG. 1, an endoscope apparatus 1 according to the present embodiment includes: an electronic endoscope 3 including a CCD 2, which is an image pickup device, as in vivo image information acquisition means or an in vivo image information acquisition section that is inserted into a body cavity to pick up an image of a tissue inside the body cavity; a light source apparatus 4 that supplies illuminating light to the electronic endoscope 3; and a video processor 7 that performs signal processing on an image pickup signal from the CCD 2 in the electronic endoscope 3 to display an endoscopic image on an observation monitor 5. The endoscope apparatus 1 has two modes: a normal light observation mode and a narrow-band light observation mode. In the below description, the normal light observation mode of the endoscope apparatus 1 is the same as a conventional normal light observation mode, and thus, a description of a configuration of the normal light observation mode will be omitted, and the narrow-band light observation mode will be described mainly.

The CCD 2 provides an image pickup section or image pickup means that receives return light of illuminating light irradiated to a subject to pick up an image of the subject.

The light source apparatus 4, which is illumination means or an illumination section, includes: a xenon lamp 11 that emits illuminating light (white light); a heat-ray cut filter 12 that blocks a heat ray of white light; a diaphragm apparatus 13 that controls an amount of white light passed through the heat-ray cut filter 12; a rotating filter 14, which is band limiting means or a band limiting section that changes the illuminating light to frame-sequential light; a collecting lens 16 that collects the frame-sequential light passed through the rotating filter 14 on an incident surface of a light guide 15 disposed inside the electronic endoscope 3; and a control circuit 17 that controls rotation of the rotating filter 14. The xenon lamp 11, the rotating filter 14 and the light guide 15 provide an illumination section or illumination means that illuminates a subject with illuminating light.

Figure 2:
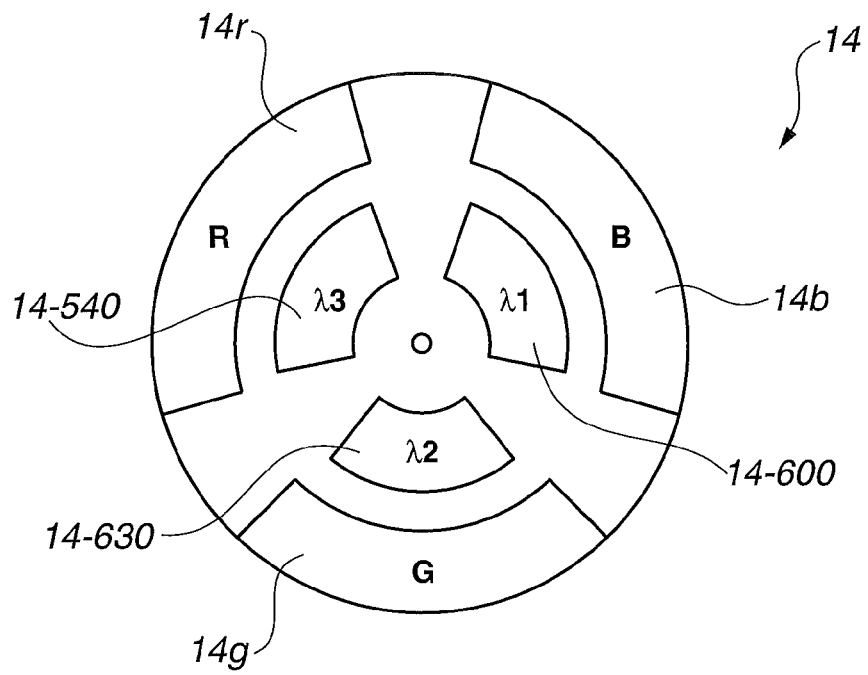
FIG. 2 is a diagram illustrating a configuration of a rotating filter 14 according to the first embodiment of the present invention.

FIG. 2 is a diagram illustrating a configuration of the rotating filter 14. The rotating filter 14 is a filter that transmits light from the xenon lamp 11, which is a light source. As illustrated in FIG. 2, the rotating filter 14, which is a wavelength band limiting section or wavelength band limiting means, is formed so as to have a disk shape and has a structure with a center thereof as a rotation axis, and includes two filter groups. On the outer circumferential side of the rotating filter 14, a R (red) filter section 14r, a G (green) filter section 14g, a B (blue) filter section 14b, which provide a filter set for outputting frame-sequential light having spectral characteristics for normal light observation, are arranged in a circumferential direction as a first filter group.

On the inner circumferential side of the rotation 14, three filters 14-600, 14-630 and 14-540, which transmit three lights with predetermined narrow-band wavelengths, are arranged in the circumferential direction as a second filter group.

The filter 14-600 is configured so as to transmit light with wavelengths of around 600 nm ($\lambda 1$) as narrow-band light. The filter 14-630 is configured so as to transmit light with wavelengths of around 630 nm ($\lambda 2$) as narrow-band light. The filter 14-540 is configured so as to transmit light with wavelengths of around 540 nm ($\lambda 3$) as narrow-band light.

Here, "around" means narrow-band light with a center wavelength of 600 nm and a distribution of wavelengths in a range of, for example, 20 nm with the wavelength of 600 nm as a center thereof in the case of the wavelengths of around 600 nm (that is, wavelengths of 590 to 610 nm in the vicinity of the wavelength of 600 nm). The same irradiates to the other wavelengths, i.e., the wavelength of 630 nm and the later-described wavelength of 540 nm.

The rotating filter 14 is arranged on an optical path from the xenon lamp 11, which is an illuminating light emitting section, to an image pickup surface of the CCD 2, and limits illuminating light so as to narrow at least two (here, three)

wavelength bands from among a plurality of wavelength bands in the illuminating light in each of the modes.

The control circuit 17 controls a motor 18 for rotating the rotating filter 14 to control the rotation of the rotating filter 14.

A rack 19a is connected to the motor 18, a non-illustrated motor is connected to a pinion 19b, and the rack 19a is attached to the pinion 19b so as to screw together. The control circuit 17 can move the rotating filter 14 in the directions indicated by arrow d by controlling rotation of the motor connected to the pinion 19b, and accordingly, the control circuit 17 controls the motor connected to the pinion 19b according to a mode switching operation by a user which will be described later so that the first filter group is positioned on the optical path in the normal light observation mode and the second filter group is positioned on the optical path in the narrow-band light observation mode.

Note that the xenon lamp 11, the diaphragm apparatus 13, the rotating filter motor 18 and the motor (not illustrated) connected to the pinion 19b are supplied with power from a power supply section 10.

Accordingly, the light source apparatus 4 provides illumination means or an illumination section that irradiates at least one illuminating light (here three narrow-band lights) having a predetermined wavelength band to a subject in the narrow-band light observation mode. Here, one from among the three illuminating lights is narrow-band light for clearly displaying blood vessels in a deep part that is 1 to 2 mm from a surface part of a mucous membrane, and the remaining two are narrow-band light for displaying blood vessels in a deeper part and narrow-band light for displaying capillary vessels in a region close to the surface part. Therefore, the light source apparatus 4 is illumination means or an illumination section that irradiates at least one illuminating light through band limiting means or a band limiting section that limits illuminating light to a first wavelength band, a second wavelength band and a third wavelength band (which will be described later) in the narrow-band light observation mode.

The video processor 7 includes a CCD drive circuit 20, which is a CCD driver, an amplifier 22, a process circuit 23, an A/D converter 24, a white balance circuit (hereinafter referred to as "W.B") 25, a selector 100, an image processing section 101, a selector 102, a γ-correction circuit 26, an enlargement circuit 27, an enhancement circuit 28, a selector 29, synchronization memories 30, 31 and 32, an image processing circuit 33, D/A converters 34, 35 and 36, a timing generator (hereinafter referred to as "T.G") 37, a mode switching circuit 42, a light-adjusting circuit 43, a light adjustment control parameter switching circuit 44, a control circuit 200, and a combining circuit 201, which is display image generation means or a display image generation section.

The CCD drive circuit 20 drives the CCD 2 provided in the electronic endoscope 3 to output a frame-sequential image pickup signal synchronized with rotation of the rotating filter 14. Also, the amplifier 22 is provided to amplify the frame-sequential image pickup signal of an image of a tissue in a body cavity picked up by the CCD 2 via an objective optical system 21 provided in a distal end of the electronic endoscope 3.

The process circuit 23 performs, e.g., correlated double sampling and denoising of the frame-sequential image pickup signal passed through the amplifier 22. The A/D converter 24 converts the frame-sequential image pickup signal passed through the process circuit 23 into a digital frame-sequential image signal.

The W.B 25 performs gain adjustment of the frame-sequential image signal digitalized by the A/D converter 24 so that, for example, an R signal in the image signal and a B signal in the image signal become equal in brightness to each other with reference to a G signal in the image signal to perform white balance processing.

Note that the white balance adjustment in the W.B 25 is performed with reference to a luminance of return light of narrow-band light with wavelengths of around 600 nm.

The selector 100 divides the frame-sequential image signal from the W.B 25 and outputs the resulting image signals to respective sections in the image processing section 101.

The image processing section 101 is an image signal processing section or image signal processing means that converts RGB image signals for normal light observation or three image signals for narrow-band light observation from the selector 100 into image signals for display. The image processing section 101 outputs image signals for the normal light observation mode or image signals for the narrow-band light observation mode to the selector 102 according to a selection signal SS from the control circuit 200 based on a mode signal.

The selector 102 sequentially outputs the image signals for normal light observation or the frame-sequential image signals for narrow-band light observation from the image processing section 101 to the γ-correction circuit 26 and the combining circuit 201.

The γ-correction circuit 26 performs γ-correction processing on the frame-sequential image signal from the selector 102 or the combining circuit 201. The enlargement circuit 27 performs processing for enlarging the frame-sequential image signal subjected to γ-correction processing by the γ-correction circuit 26. The enhancement circuit 28 performs contour enhancement processing on the frame-sequential image signal subjected to the enlargement processing by the enlargement circuit 27. The selector 29 and the synchronization memories 30, 31 and 32 are provided to synchronize the frame-sequential image signal from the enhancement circuit 28.

The image processing circuit 33 reads the respective frame-sequential image signals stored in the synchronization memories 30, 31 and 32 to perform, e.g., moving image color shift correction processing. The D/A converters 34, 35 and 36 convert the image signals from the image processing circuit 33 into RGB analog video signals and output the analog video signals to the observation monitor 5. The T.G 37 receives an input of a synchronization signal synchronized with rotation of the rotating filter 14 from the control circuit 17 in the light source apparatus 4, and outputs various timing signals to the respective circuits in the video processor 7.

Also, in the electronic endoscope 2, a mode selection switch 41 for switching between the normal light observation mode and the narrow-band light observation mode is provided, and an output of the mode selection switch 41 is outputted to a mode switching circuit 42 in the video processor 7. The mode switching circuit 42 in the video processor 7 outputs a control signal to the light adjustment control parameter switching circuit 44 and the control circuit 200. The light-adjusting circuit 43 is configured so as to control the diaphragm apparatus 13 in the light source apparatus 4 based on a light adjustment control parameter from the light adjustment control parameter switching circuit 44 and the image pickup signal passed through the process circuit 23 to perform proper brightness control. In other words, the light-adjusting circuit 43 generates a light adjustment reference signal according to the observation mode and outputs the light adjustment reference signal to the diaphragm apparatus 13, thereby controlling a diaphragm in the diaphragm apparatus 13 so that proper image signals can be obtained in each of the normal light observation mode and the narrow-band light observation mode.

The respective circuits in the video processor 7 perform predetermined processing according to the designated mode. As a result of processing according to the normal light observation mode or the narrow-band light observation mode being performed, an image for normal light observation or a narrow-band light observation image is displayed on the observation monitor 5.

The video processor 7 provides image signal processing means or an image signal processing section that generates an image signal based on an image pickup signal from the CCD 2, which is image pickup means or an image pickup section.

As described later, the observation monitor 5 is display means or a display section that performs image display based on an image signal of relatively-thick blood vessels with diameters ranging from around 1 to 2 mm in a deep part of a mucous membrane that is around 1 to 2 mm from a surface part of the mucous membrane.

(Overall Flow of Processing for Narrow-Band Light Observation)

Next, a rough overall flow of narrow-band light observation in the present embodiment will briefly be described.

Figure 3:
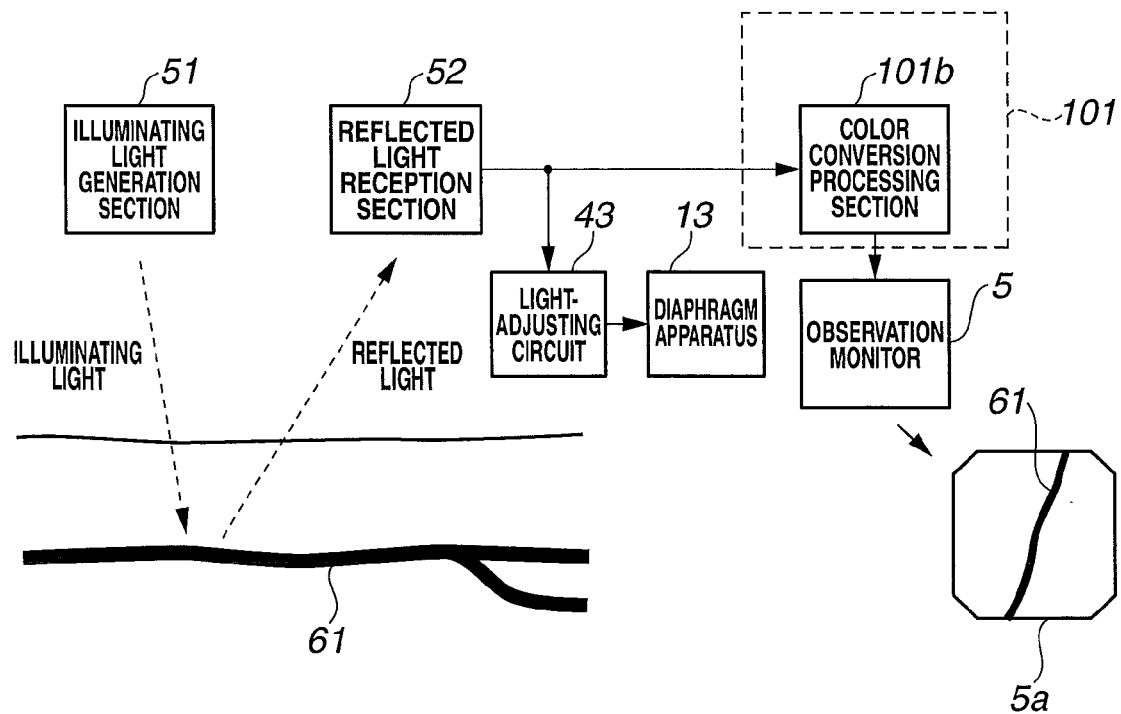
FIG. 3 is a diagram for describing an overall flow of processing in a narrow-band light observation according to the first embodiment of the present invention.

FIG. 3 is a diagram for describing the overall flow of processing in a narrow-band light observation according to the present embodiment.

A surgeon inserts an insertion portion of the endoscope into a body cavity and positions a distal end portion of the insertion portion of the endoscope in the vicinity of a lesion site in the normal light observation mode. When the surgeon recognizes the lesion site to be treated, the surgeon operates the mode selection switch 41 to switch the endoscope apparatus 1 to the narrow-band light observation mode in order to observe blood vessels in a deep part, the blood vessels being relatively thick, having diameters of, for example, 1 to 2 mm and running from a submucosal layer to an intrinsic muscle layer.

In the narrow-band light observation mode, the control circuit 17 in the endoscope apparatus 1 moves a position of the rotating filter 14 by controlling the motor connected to the pinion 19b so as to make light passed through the second filter group exit from the light source apparatus 4. Furthermore, the control circuit 200 also controls various circuits in the video processor 7 so as to perform image processing for observation with narrow-band wavelengths.

As illustrated in FIG. 3, in the narrow-band light observation mode, illuminating light with narrow-band wavelengths from an illuminating light generation section 51 is made to exit from the distal end portion of the insertion portion of the endoscope 3, penetrates a mucous membrane layer and is irradiated to blood vessels 61 running in a submucosal layer and an intrinsic muscle layer. Here, the illuminating light generation section 51 includes, e.g., the light source apparatus 4, the rotating filter 14 and the light guide 15, and makes illuminating light exit from the distal end of the insertion portion of the endoscope. Upon rotation of the rotating filter 14, narrow-band light with wavelengths of around 600 nm, narrow-band light with wavelengths of around 630 nm and narrow-band light with wavelengths of around 540 nm are made to exit from the light source apparatus 4 successively in order and irradiated to an object.

Each of reflected light of the narrow-band light with wavelengths of around 600 nm, reflected light of the narrow-band light with wavelengths of around 630 nm and reflected light of the narrow-band light with wavelengths of around 540 nm is received by a reflected light reception section 52, which is the CCD 2. The CCD 2 outputs an image pickup signal for each reflected light and supplies the image pickup signals to the selector 100 via, e.g., the amplifier 22. The selector 100 holds a first image signal P1 with wavelengths of around 600 nm, a second image signal P2 with wavelengths of around 630 nm and a third image signal P3 with wavelengths of around 540 nm in response to predetermined timings from the T.G 37 and supplies the signals to the image processing section 101. The image processing section 101 includes a color conversion processing section 101b for the narrow-band light observation mode.

Accordingly, the video processor 7 generates image signals based on the first image signal P1, the second image signal P2 and the third image signal P3 with a third wavelength band having a peak wavelength of a spectral characteristic in a wavelength band providing a higher value in absorption characteristic than that of the first image signal P1 and outputs the image signals to the observation monitor 5.

Furthermore, the respective image pickup signals are inputted also to the light-adjusting circuit 43. As described later, the light-adjusting circuit 43 generates a light adjustment reference signal based on the observation mode and outputs the light adjustment reference signal to the diaphragm apparatus 13.

In ESD in which a submucosal layer at which a lesion site exists at an inner wall of a digestive tract such as, for example, a stomach, an esophagus or a large intestine is dissected and removed using the endoscope apparatus 1, a surgeon needs to be careful not to cut relatively-thick blood vessels in the tissue by, e.g., an electrosurgical knife. When the surgeon sets the endoscope apparatus 1 to the narrow-band light observation mode, blood vessels below a surface of a body tissue can clearly be drawn.

The color conversion processing section 101b in the image processing section 101 in FIG. 1 supplies image signals to the selector 102 with the respective image signals assigned to respective R, G and B channels of the observation monitor 5. As a result, on a screen 5a of the observation monitor 5, relatively-thick blood vessels 61 in a deep part of a mucous membrane are displayed with high contrast. Accordingly, the surgeon can perform ESD of the lesion site while paying attention to the blood vessels 61 running in a submucosal layer and an intrinsic muscle layer, which are displayed on the observation monitor 5.

Figure 4:
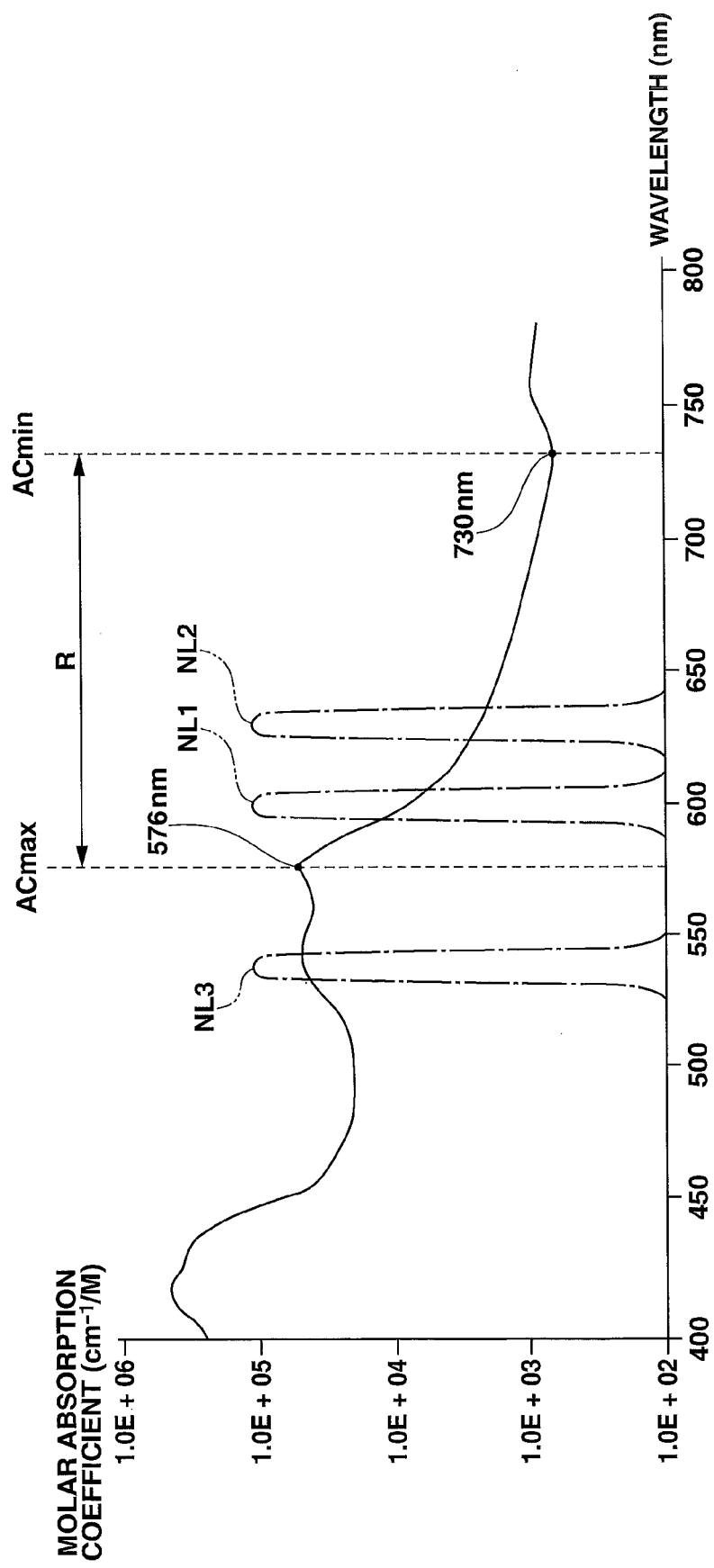
FIG. 4 is a diagram illustrating a light absorption characteristic of venous blood according to the first embodiment of the present invention.

Here, a light absorption characteristic of venous blood will be described. FIG. 4 is a diagram illustrating a light absorption characteristic of venous blood. In FIG. 4, the ordinate axis represents a molar absorption coefficient ($cm^{-1}/M$) and the abscissa axis represents wavelength. Although illuminating light including three narrow-band lights is affected by a scattering characteristic of a body tissue itself, the scattering characteristic of a body tissue itself substantially monotonously decreases relative to an increase in wavelength, and thus, a description will be provided considering FIG. 4 as indicating an absorption characteristic of a body tissue.

In general, venous blood contains oxygenated hemoglobin ($HbO_2$) and reduced hemoglobin (Hb) (hereinafter collectively referred to simply as hemoglobin) at a ratio of approximately 60:40 to 80:20. Although light is absorbed by hemoglobin, the absorption coefficient varies depending on the wavelength of the light. FIG. 4 indicates a light absorption characteristic of venous blood for each of wavelengths from 400 nm to approximately 800 nm, and in a range from 550 to 750 nm, the absorption coefficient indicates a maximal value at a point of a wavelength of approximately 576 nm and a minimal value at a point of a wavelength of 730 nm.

In the narrow-band light observation mode, three narrow-band lights are irradiated and return light of each of the three lights is received in the CCD 2.

Narrow-band light with wavelengths of around 600 nm (hereinafter referred to as "first narrow-band light NL1") is light with a wavelength band within a wavelength band R for from a maximal value ACmax (here, an absorption coefficient for a wavelength of 576 nm) to a minimal value ACmin (here, an absorption coefficient for a wavelength of 730 nm) in an absorption characteristic of hemoglobin.

Narrow-band light with wavelengths of around 630 nm (hereinafter referred to as "second narrow-band light NL2") is also light within the wavelength band R for from the maximal value ACmax to the minimal value ACmin in the absorption characteristic of hemoglobin, but is light with a wavelength band including wavelengths longer than those of the first narrow-band light NL1, providing low absorption coefficients and providing a suppressed scattering characteristic of a body tissue. Suppressed scattering characteristic means that a scattering coefficient decreases toward the long wavelength side.

In other words, the light source apparatus 4 irradiates the first illuminating light NL1 having a peak wavelength of a spectral characteristic between a wavelength band providing the maximal value ACmax and a wavelength band for the minimal value ACmin in an absorption characteristic of a body tissue.

Furthermore, here, the light source apparatus 4 also irradiates the second illuminating light NL2 having a peak wavelength of a spectral characteristic providing a value in the absorption characteristic that is lower than that of the image signal P1 of the first illuminating light NL1 and providing a suppressed scattering characteristic of a body tissue.

Furthermore, the light source apparatus 4 also irradiates narrow-band light with wavelengths of around 540 nm (hereinafter also referred to as "third narrow-band light NL3"). The third narrow-band light NL3 is light with a wavelength band outside the wavelength band R for from the maximal value ACmax to the minimal value ACmin in the absorption characteristic of hemoglobin and is illuminating light that can penetrate a predetermined distance from a surface part of a mucous membrane surface of a subject.

The CCD 2 outputs an image pickup signal for each of images of the three narrow-band lights. Accordingly, the respective images each include a plurality of pixel signals based on the respective return lights of the first narrow-band light NL1, the second narrow-band light NL2 and the third narrow-band light NL3.

Figure 5:
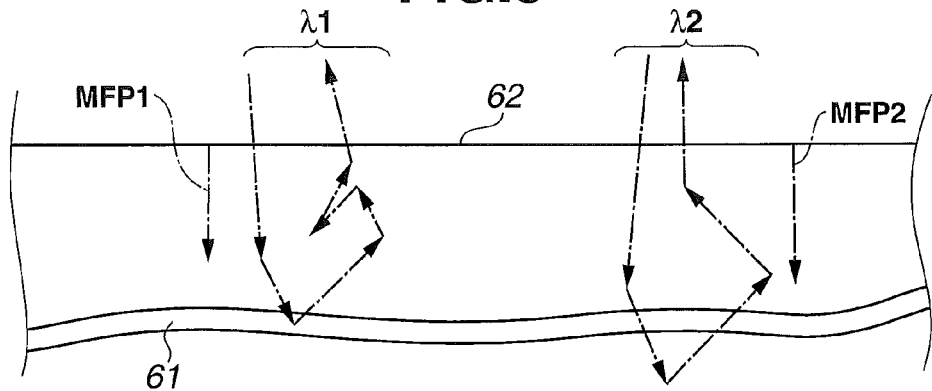
FIG. 5 is a diagram for describing propagated volumes of first narrow-band light NL1 ($\lambda 1$) and second narrow-band light NL2 ($\lambda 2$) inside a body tissue, according to the first embodiment of the present invention.

Furthermore, light propagation of the first narrow-band light NL1 and the second narrow-band light NL2, which are included in illuminating light, inside a body tissue will be described. FIG. 5 is a diagram for describing light propagation volumes of the first narrow-band light NL1 ($\lambda$1) and the second narrow-band light NL2 ($\lambda$2) inside a body tissue. The first narrow-band light NL1 and the second narrow-band light NL2 each repeat a multiple scattering process inside the body tissue, and as a result, exit from the mucous membrane surface as return light. The first narrow-band light NL1 and the second narrow-band light NL2 have respective mean free paths MFP1 and MFP2. The mean free path MFP1 of the first narrow-band light NL1 is shorter than the mean free path MFP2 of the second narrow-band light NL2.

As illustrated in FIG. 5, the first narrow-band light NL1 with wavelengths of around 600 nm ($\lambda$1) reaches a vicinity of a blood vessel 61, and the second narrow-band light NL2 with wavelengths of around 630 nm ($\lambda$2) reaches a position slightly deeper than the blood vessel 61. Accordingly, use of the first narrow-band light NL1 enables display of relatively-thick blood vessels with diameters of 1 to 2 mm, which exist in a relatively-deep part that is 1 to 2 mm below a surface of a mucous membrane of a living body.

Furthermore, as described later, use of the second narrow-band light NL2 with wavelengths of around 630 nm ($\lambda$2) also enables display of thicker blood vessels in a deeper part.

Here, an image signal of narrow-band light with wavelengths of around 600 nm is generated; however, as described above, because of, e.g., variation in diameter of blood vessels as well as variation in depth, generation of an image signal with a wavelength band, such as illustrated in FIG. 4, having a predetermined wavelength width and a peak wavelength of a spectral characteristic between a wavelength band providing a maximal value in an absorption characteristic of a body tissue and a wavelength band for a minimal value enables display of blood vessels in a deep part of a mucous membrane.

Accordingly, it is preferable that the wavelength band of the first narrow-band light NL1 have a peak wavelength of a spectral characteristic in a range of from a wavelength of 585 nm to a wavelength of 615 nm.

Figure 19:
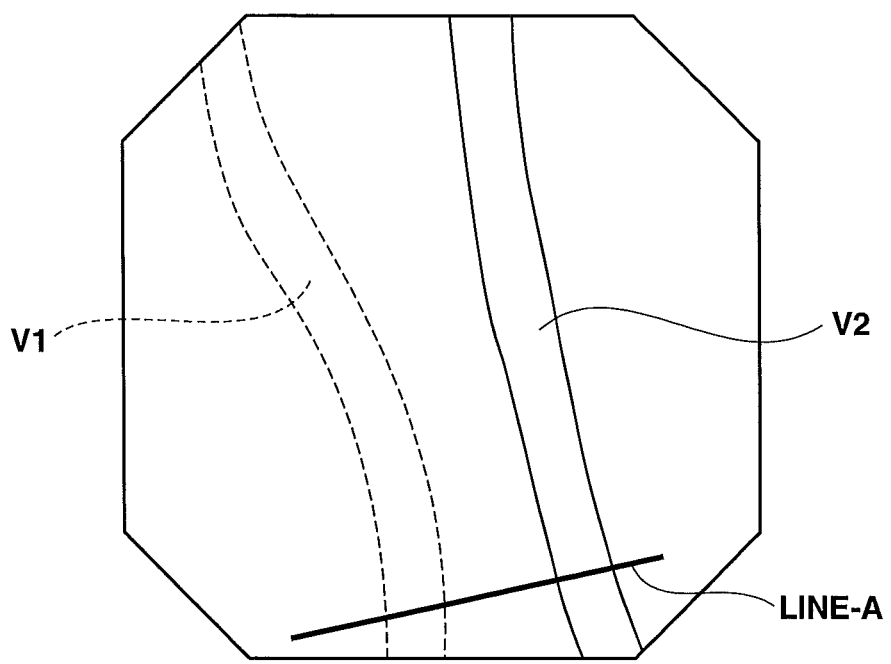
FIG. 19 is a schematic diagram of an image taken of an inside of an abdominal cavity of an animal using a spectral endoscope apparatus capable of chronologically irradiating narrow-band illuminating light while a center wavelength thereof is shifted in increments of 10 nm.

FIG. 19 is a schematic diagram of an image picked up of an inside of an abdominal cavity of an animal using a spectral endoscope apparatus capable of chronologically irradiating narrow-band illuminating light while a center wavelength thereof is shifted in increments of 10 nm. More specifically, an image with respective monochromatic images of 540 nm, 600 nm and 630 nm assigned to the B channel, the G channel and the R channel, respectively, is illustrated. A blood vessel V1 and a blood vessel V2 in the image are thick blood vessels running from the upper left side to the lower right side in the image. The blood vessel V1 is positioned deeper from the mucous membrane surface than the blood vessel V2. Here, a total of 15 monochromatic images were taken in increments of 10 nm for a range from 540 to 680 nm.

Figure 20:
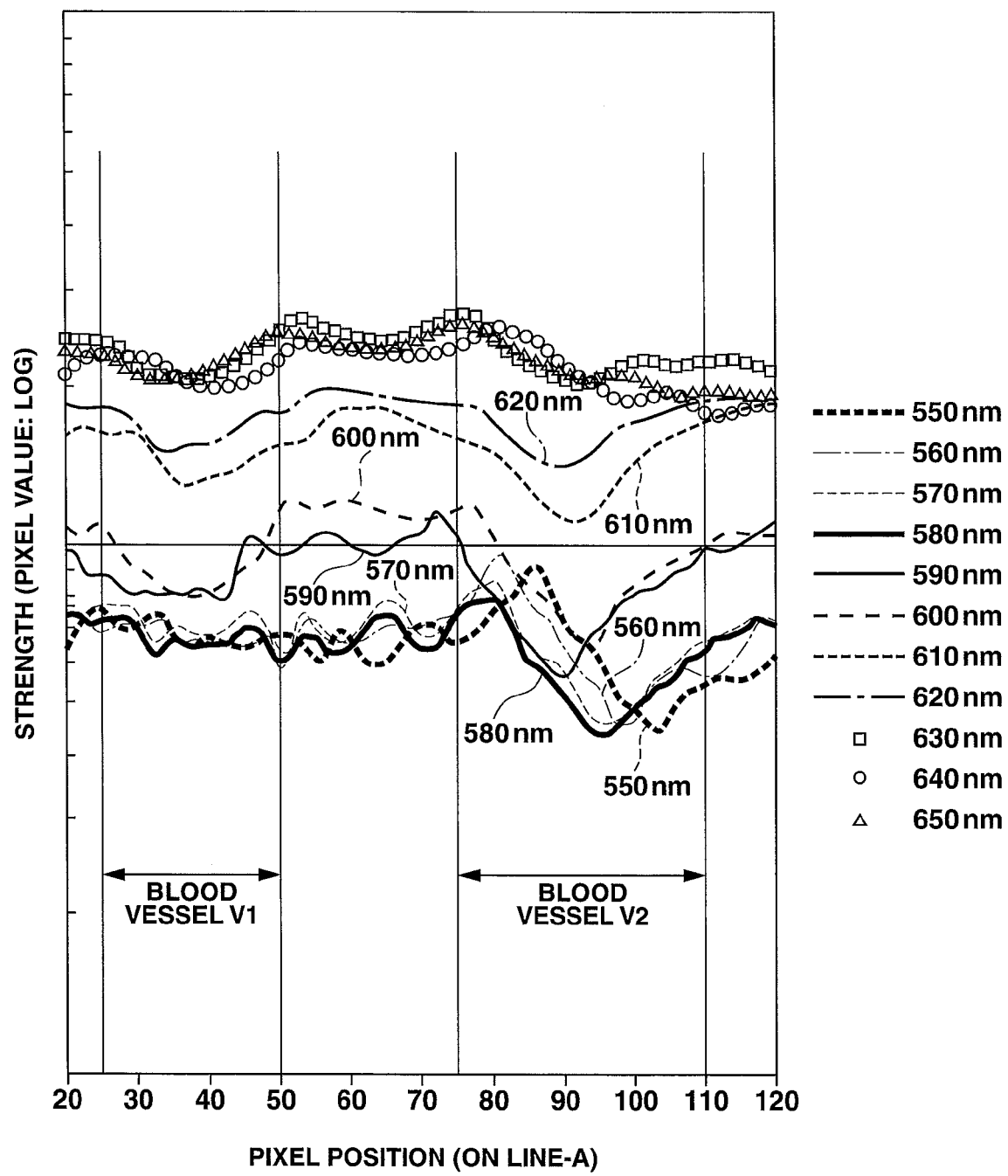
FIG. 20 is a graph indicating strengths on Line-A (pixel values expressed in logarithmic scale) in each image of a plurality of monochromatic images in FIG. 19 as an ordinate axis.

FIG. 20 is a graph indicating strength on Line-A (pixel values expressed in logarithmic scale) in each of the plurality of monochromatic images in FIG. 19 as the ordinate axis. The abscissa axis in FIG. 20 indicates positions of pixels on Line-A in each of the images. The positions of the pixels of the blood vessel V1 exist in around 25 to 50 and the positions of the pixels of the blood vessel V2 exist in around 75 to 110. It can be understood from FIG. 20 that illumination wavelengths at which the strengths have been attenuated for both the blood vessel V2, which exists in a relatively-shallow part, and the blood vessel V1, which is positioned in a deep part, that is, wavelengths at which illuminating light is strongly absorbed by the blood vessel V1 and the blood vessel V2 are approximately 590 to 620 nm.

Accordingly, in order to detect blood vessels existing in a part ranging from a relatively-shallow part to a deep part, narrow-band light of approximately 590 to 620 nm provides important wavelength information. The blood vessel V1 exists in a part around 1 to 2 mm deep from the mucous membrane surface. Note that the results of the present test are substantially consistent with the aforementioned results of theoretical calculations according to the Beer-Lambert law (use of narrow-band light in a range of 15 nm shorter and longer than a wavelength 600 of nm enables display of relatively-thick blood vessels with high contrast).

As described above, the light source apparatus 4 also irradiates the narrow-band light NL2, which is illuminating having a peak wavelength of a spectral characteristic that provides a low value in characteristic of absorption of return light of the first narrow-band light NL1, provides a suppressed scattering characteristic of a body tissue and has a wavelength band different from the wavelength band of the first narrow-band light NL1, and a third narrow-band light NL3 capable of penetrating a predetermined distance from a surface part of a subject.

The narrow-band light NL2 is narrow-band light for obtaining an image of blood vessels in a part deeper than the blood vessel displayed using the narrow-band light NL1, and the narrow-band light NL3 is narrow-band light for obtaining an image of capillary vessels in a surface part.

Figure 6:
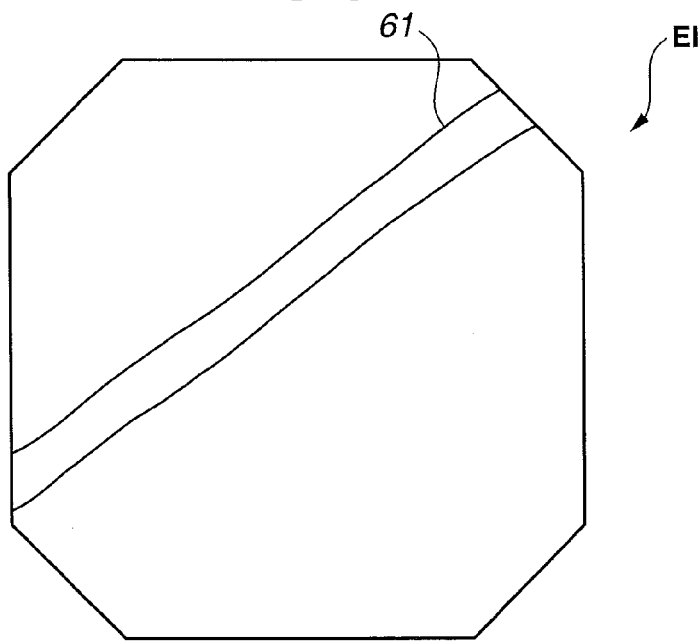
FIG. 6 is a diagram illustrating an example endoscopic image for describing example display of a blood vessel in an endoscopic image in a narrow-band light observation mode, according to the first embodiment of the present invention.

Next, processing in the image processing section 101 will be described. FIG. 6 is a diagram illustrating an example endoscopic image for describing example display of blood vessels in an endoscopic image in the narrow-band light observation mode.

In the normal light observation mode, within a picked-up endoscopic image EI, blood vessels in a deep part that is 1 to 2 mm from a surface part are not displayed or is hard to be displayed in the endoscopic image EI on the observation monitor 5.

On the other hand, in the narrow-band light observation mode, if a blood vessel exists in a deep part within a picked-up endoscopic image EI, as illustrated in FIG. 6, the blood vessel 61 is displayed in the endoscopic image EI.

Accordingly, the image processing section 101 provides image output means or an image output section that after pickup of an image by the image pickup means or the image pickup section, outputs an image signal P1 ($\lambda$1) with a predetermined wavelength band with a peak wavelength of a spectral characteristic between a wavelength band providing a maximal value ACmax and a wavelength band for a minimal value ACmin in an absorption characteristic of a body tissue.
(Processing in Light-Adjusting Circuit)

The light-adjusting circuit 43 generates a light adjustment reference signal Y according to the observation mode. A mode signal for a mode designated by an operation of the mode selection switch 41 by a user is inputted to the light adjustment control parameter switching circuit 44 via the mode switching circuit 42, and the light adjustment control parameter switching circuit 44 outputs light adjustment control parameters according to the observation mode to the light-adjusting circuit 43.

The light-adjusting circuit 43 generates a light adjustment reference signal Y based on three image pickup signals from the process circuit 23 and the light adjustment control parameters from the light adjustment control parameter switching circuit 44. Hereinafter, a light adjustment reference signal Y in the normal light observation mode is referred to as a light adjustment reference signal Yw, and a light adjustment reference signal Y in the narrow-band light observation mode is referred to as a light adjustment reference signal Yn.

In the normal light observation mode, the light-adjusting circuit 43 generates a light adjustment reference signal Yw based on equation (1) below.

$$Yw=0.3Ib(R)+0.6Ib(G)+0.1Ib(B) \quad \text{Equation (1)}$$

Here, Ib(R) is a luminance value of a R signal, Ib(G) is a luminance value of a G signal, and Ib(B) is a luminance value of a B signal. Each luminance value is, for example, an average value of each luminance value for one frame. As indicated in equation (1), in the normal light observation mode, the respective R, G and B signals are multiplied by respective light adjustment control parameters. Here, "0.6", which is a largest weight, is provided to the G signal.

In the narrow-band light observation mode, the light-adjusting circuit 43 generates a light adjustment reference signal YnW based on equation (2) below.

$$Yn=0.3Ib(630)+0.6Ib(600)+0.1Ib(540) \quad \text{Equation (2)}$$

Here, Ib(630) is a luminance value of a narrow-band light signal with wavelengths of around 630 nm, Ib(600) is a luminance value of a narrow-band light signal with wavelengths of around 600 nm, and Ib(540) is a luminance value of a narrow-band light signal with wavelengths of around 540 nm. Each luminance value is, for example, an average value of each luminance value for one frame. As indicated in equation (2), in the narrow-band light observation mode, the respective narrow-band signals NL1, NL2 and NL3 are multiplied by respective light adjustment control parameters. Here, "0.6", which is a largest weight, is provided to the narrow-band light signal with wavelengths of around 600 nm.

Here, the values of the respective light adjustment control parameters in equation (2) are 0.6, 0.3 and 0.1, which are the same as those of equation (1), but may be different from those of equation (1).

As described above, in equation (1), the light adjustment reference signal Yw is generated with a largest weight provided to the G signal. On the other hand, in equation (2), the light adjustment reference signal Yn is generated with a largest weight provided to the narrow-band signal with wavelengths of around 600 nm.

Here, in the narrow-band light observation mode, the light-adjusting circuit 43 multiples an image signal of the first narrow-band light NL1 with wavelengths of around 600 nm, which is a most important signal, by a weight coefficient larger than those of the other image signals to generate a light adjustment reference signal Yn, and controls the diaphragm in the diaphragm apparatus 13 based on the light adjustment reference signal Yn.

In other words, the light-adjusting circuit 43 provides light adjusting means or a light adjusting section that, based on a first image signal P1 with a first wavelength band having a peak wavelength of a spectral characteristic between a wavelength band providing a maximal value and a wavelength band for a minimal value in an absorption characteristic of a body tissue of a subject and a second image signal P2 of a second wavelength band having a peak wavelength of a spectral characteristic providing a value in the absorption characteristic that is lower than that of the first image signal P1 and providing a suppressed scattering characteristic of the body tissue such as illustrated in FIG. 4, provides a weight larger than that of the second image signal P2 to the first image signal P1 to calculate a light adjustment signal for adjusting an amount of light in the light source apparatus 4, which is illumination means or an illumination section, and outputs the light adjustment signal.

In a test conducted by the applicant, use of the above-described light adjustment reference signal Yn in the narrow-band light observation mode enabled obtainment of an endoscopic image with proper light adjustment subjected thereto. In the test, an image of the blood of a pig was picked up in the narrow-band light mode; however, when a light adjustment reference signal was generated with a largest weight added to an image signal with a wavelength band of a conventional G signal, luminance values of a red image of the blood were partially saturated.

On the other hand, as in the present embodiment, when a light adjustment reference signal Yn was generated with a weight larger than those of the other image signals provided to an image signal of the first narrow-band light NL1 with wavelengths of around 600 nm, luminance values of a red image of the blood were not saturated.

As described above, the light-adjusting circuit 43 weighs luminance values of the respective narrow-band lights based on light adjustment parameters according to the observation mode to generate a light adjustment reference signal, and in particular, in the narrow-band light observation mode, provides a largest weight to the narrow-band light with wavelengths of around 600 nm to generate a light adjustment reference signal Yn. Note that a light adjustment reference signal Yn may be calculated with 630 changed to 630×α', 600 to 600×β' and 540 to 540×γ' as equation (3') instead of equation (2). Here, α', β' and γ' are weight coefficients provided to the respective image signals in the later-described color conversion processing section.

Next, processing in the image processing section 101 will be described. The image processing section 101, which includes the color conversion processing section 101b, performs color conversion processing.

(Color Conversion Processing in Image Processing Section)

Next, processing in the color conversion processing section 101b will be described. A first image signal P1 (λ1), a second image signal P2 (λ2) and a third image signal P3 (λ3) are inputted to the color conversion processing section 101b.

Figure 7:
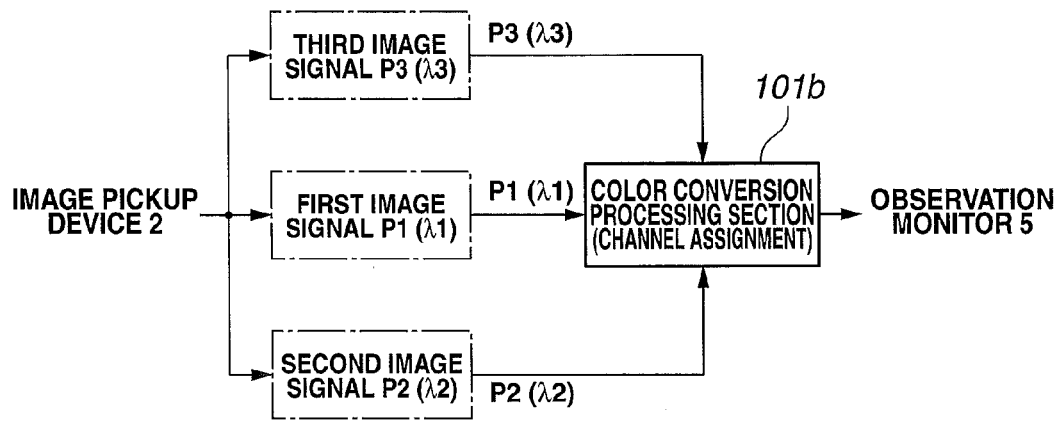
FIG. 7 is a block diagram for describing a configuration of an image processing section 101 according to the first embodiment of the present invention.

FIG. 7 is a block diagram for describing a configuration of the image processing section 101. Three image signals from the image pickup device are inputted to the color conversion processing section 101b. The color conversion processing section 101b subjects color conversion processing on the first image signal P1 (λ1), the second image signal P2 (λ2) and the third image signal P3 (λ3) by channel assignment and outputs the resulting image signals to the observation monitor 5.

In order to display a blood vessel 61 in a deep part with high contrast by the narrow-band light NL1 with wavelengths of around 600 nm, the color conversion processing section 101b assigns the first image signal P1(λ1) to the three BGR channels so as to output the first image signal P1(λ1) to the observation monitor 5 as a monochromatic image. Note that, if a monochromatic image display circuit is provided, the first image signal P1(λ1) may be inputted to the monochromatic image display circuit to output the first image signal P1(λ1) to the observation monitor 5 as a monochromatic image.

Consequently, in the narrow-band light observation mode, the blood vessel 61 illustrated in FIG. 6 is displayed with high contrast on the endoscopic image EI.

Accordingly, the image processing section 101 provides image output means or an image output section that outputs a first image signal P1(λ1) based on an image signal obtained as a result of an image of return light being picked up by the CCD 2, which is image pickup means or an image pickup section.

Note that, in the color conversion processing section 101b, color conversion processing may be performed using at least one of the second image signal P2 (λ2) and the third image signal P3 (λ3) in addition to the first image signal P1 (λ1). Modifications 1 to 3 of the color conversion processing in the color conversion processing section 101b will be described.

First, modification 1 will be described.

In a color conversion processing section 101b in modification 1, processing for assigning a first image signal P1 (λ1), a second image signal P2 (λ2) and a third image signal P3 (λ3) to respective G, R and B channels is performed.

Here, for example, in the color conversion processing section 101b, processing according to equation (3) below is performed to assign a luminance value 1 mA (λ1) of the first image signal P1(λ1), a luminance value lm (λ2) of the second image signal P2 (λ2) and a luminance value lm (λ3) of the third image signal P3 (λ3) are assigned to the respective G, R and B channels.

$$\begin{pmatrix} B \\ G \\ R \end{pmatrix} = \begin{pmatrix} 1 & 0 & 0 \\ 0 & 1 & 0 \\ 0 & 0 & 1 \end{pmatrix} \begin{pmatrix} \mathrm{Im}(\lambda 3) \\ \mathrm{Im}A(\lambda 1) \\ \mathrm{Im}(\lambda 2) \end{pmatrix} \quad \text{Equation (3)}$$

According to equation (3), a relatively-thick blood vessel 61 in a deep part is displayed in somewhat reddish color, which can easily be recognized by a surgeon.

Figure 8:
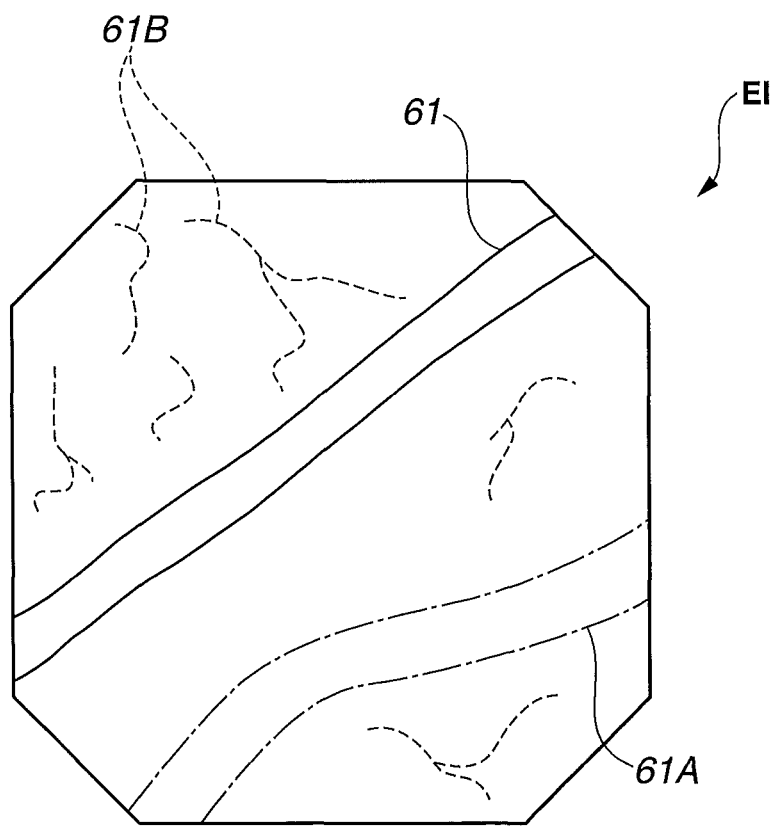
FIG. 8 is a diagram for describing example display of an endoscopic image using three image signals, according to the first embodiment of the present invention.

FIG. 8 is a diagram for describing example display of an endoscopic image using three image signals. A blood vessel 61 in a deep part, which is indicated by solid lines, is displayed in somewhat reddish color, and a blood vessel 61A (indicated by alternate long and short dash lines) deeper than the blood vessel 61 is displayed in blue, and a capillary vessel 61B indicated by dotted lines is displayed in substantially yellow color. In particular, a mucous membrane of a body tissue, and furthermore, blood on a surface of the mucous membrane are also displayed in substantially yellow color.

Here, third narrow-band light NL3 is light with wavelengths of around 540 nm, but may be light with shorter wavelengths, for example, light with wavelengths of around 460 nm or light with wavelengths of around 415 nm, in order to obtain surface layer information.

As a result of assigning narrow-band light NL1 with wavelengths of around 600 nm, which is highly absorbed, to the G channel and narrow-band light NL2 with wavelengths of around 630 nm, which is less absorbed relative to the narrow-band light NL1, to the R channel, the respective blood vessels 61 and 61A in a deep part can be displayed in colors (somewhat reddish colors) different from a surface color of the body tissue.

Also, even if there is blood on the mucous membrane surface of the body tissue due to bleeding, the blood vessel 61 in the deep part and the blood vessel 61A in the deeper part are displayed in colors different from that of the blood, which can easily be viewed by a surgeon.

Also, the first image signal P1 (λ1), the second image signal P2 (λ2) and the third image signal P3 (λ3) may be assigned to the respective G, B and R channels. In such case, a display image similar to an image obtained by the color conversion processing according to equation (3) above can be displayed on the observation monitor 5 by making, e.g., strength adjustment of the respective image signals by, e.g., multiplying each of the value in the matrix in equation (3) by a coefficient.

Note that, in the color conversion processing 101b, equation (4) below can be used instead of equation (3) above.

$$\begin{pmatrix} B \\ G \\ R \end{pmatrix} = \begin{pmatrix} 1 & 0 & 0 \\ 1 & 0 & 0 \\ 0 & 1 & 0 \end{pmatrix} \begin{pmatrix} \mathrm{Im}(\lambda 3) \\ \mathrm{Im}A(\lambda 1) \\ \mathrm{Im}(\lambda 2) \end{pmatrix} \quad \text{Equation (4)}$$

According to equation (4), the blood vessel 61 in the deep part is indicated in somewhat blue or blue-green and capillary vessels at the surface are displayed in reddish color, which can easily be recognized by a surgeon.

Furthermore, in the color conversion processing 101b, equation (5) below may be used instead of equation (3) above.

$$\begin{pmatrix} B \\ G \\ R \end{pmatrix} = \begin{pmatrix} 1 & 0 & 0 \\ 0.5 & 0.5 & 0 \\ 0 & 1 & 0 \end{pmatrix} \begin{pmatrix} \mathrm{Im}(\lambda 3) \\ \mathrm{Im}A(\lambda 1) \\ \mathrm{Im}(\lambda 2) \end{pmatrix} \quad \text{Equation (5)}$$

Furthermore, in the color conversion processing 101b, equation (6) below may be used instead of equation (3) above. Here, α has a numerical value of approximately 1.0 to 1.5, β has a numerical value of approximately 2.0 to 2.6, and γ has a numerical value of approximately 2.5 to 3.3 (for example, α:β:γ=0.56:1.00:1.17). In this case, a color of blood vessels in a deep part is blue-green and a color of a mucous membrane is similar to that of normal observation, which can easily be observed by a surgeon with no stress. Furthermore, where α has a numerical value of approximately 2.3 to 2.7, β has a numerical value of approximately 2.3 to 2.7 and γ has a numerical value of approximately 1.7 to 2.1 (for example, α:β:γ=1.00:1.00:0.76), blood vessels in a surface and a deep part can easily be observed.

$$\begin{pmatrix} B \\ G \\ R \end{pmatrix} = \begin{pmatrix} \alpha & 0 & 0 \\ \beta & 0 & 0 \\ 0 & \gamma & 0 \end{pmatrix} \begin{pmatrix} \mathrm{Im}(\lambda 3) \\ \mathrm{Im}A(\lambda 1) \\ \mathrm{Im}(\lambda 2) \end{pmatrix} \quad \text{Equation (6)}$$

Another example of channel assignment in the color conversion processing section 101b will be described. For example, during a treatment, the narrow-band light with wavelengths of around 540 nm may be assigned to the B channel, the narrow-band light with wavelengths of around 630 nm to the G channel and the narrow-band light with wavelengths of around 600 nm to the R channel instead of equation (3) above.

Also, during diagnosis, the narrow-band light with wavelengths of around 540 nm may be assigned to the B channel and the G channel and the narrow-band light with wavelengths of around 600 nm or the narrow-band light with wavelengths of around 630 nm to the R channel.

Here, color balance adjustment will be described.

For example, where the narrow-band light with wavelengths of around 540 nm is assigned to the B channel, the narrow-band light with wavelengths of around 600 nm is assigned to the G channel and narrow-band light with wavelengths of around 630 nm is assigned to the R channel as with equation (3), it is desirable to amplify the signal for the B channel relative to the signal for R channel. The signal strength of the narrow-band light with wavelengths of around 600 nm is not corrected, but the remaining two signals are adjusted so that the signal strength of the narrow-band light with wavelengths of around 540 nm assigned to the B channel becomes 0.7 to 2.5 times the signal strength of the narrow-band light with wavelengths of around 630 nm assigned to the R channel. Note that color conversion processing may be performed after the color balance adjustment is performed, or the color balance adjustment may be performed after color conversion processing.

Accordingly, the color conversion processing section 101b provides color balance adjustment means or a color balance-adjusting section that performs color balance adjustment by amplifying the third image signal P3 by a predetermined amount relative to the second image signal P2 for in vivo information discrimination.

Consequently, differences in color among a mucous membrane, fiber tissues in white, bleeding in yellow, carbonized areas in black and thick blood vessels in colors of from red to magenta become more conspicuous, enabling provision of a display image that makes a surgeon perform treatment or diagnosis more easily.

The color balance-adjusting circuit for color balance adjustment such as described above may be provided upstream of the W.B 25 in FIG. 1. In such case, where illuminating light of the narrow-band light with wavelengths of around 540 nm and illuminating light of the narrow-band light with wavelengths of around 630 nm are substantially equal to each other in strength, the color balance-adjusting circuit multiplies the signal of the narrow-band light with wavelengths of around 540 nm assigned to the B channel by around 0.7 to 1.5 and also multiplies the signal of the narrow-band light with wavelengths of around 630 nm assigned to the R channel by around 0.6 to 1.0.

Note that color balance adjustment may be performed in the color conversion processing section 101b, may be performed by adjusting the strength of the illuminating light in the light source apparatus 4 or may be performed by adjusting a transmittance of each color of a color filter in the image pickup device.

Next, modification 2 will be described. Here, unless specifically stated, gain adjustment for color balance adjustment is not performed, that is, each gain is 1.

In modification 2, two image signals from among three image signals are assigned to channels.

As an example, in a color conversion processing section 101b according to modification 2, processing for assigning a first image signal P1 (λ1) to G and B channels and assigning a second image signal P2 (λ2) to an R channel may be performed.

In the case of such assignment, in an endoscopic image EI, bleeding or blood vessels in a deep part are displayed in somewhat reddish color, and a mucous membrane is displayed in whitish color, and surface capillary vessels are not displayed or are hard to be displayed.

As modification 3, in a color conversion processing section 101b, processing for assigning a first image signal P1 (λ1) to an R channel and assigning a third image signal P3 (λ3) to G and B channels may be performed.

In the case of such assignment, in an endoscopic image EI, bleeding and a mucous membrane are displayed in somewhat reddish color, and blood vessels in a deep part is displayed in green color.

Also, in this case, gain adjustment of the respective channels may be performed. For example, if gains of the G and B channels to which the third image signal P3 (λ3) is assigned is made to be around 1.3 to 1.5 times a gain of the R channel to which the first image signal P1 (λ1) is assigned, bleeding and a mucous membrane are displayed in reddish color and blood vessels in a deep part are displayed in blue to green colors.

For example, if the gains of the G and B channels to which the third image signal P3 (λ3) is assigned and the gain of the R channel to which the first image signal P1 (λ1) is assigned are set to be higher in the order of B, R and G, bleeding and a mucous membrane are displayed in brown and blood vessels in a deep part are displayed in blue to green colors.

Furthermore, for example, if the gains of the G and B channels to which the third image signal P3 (λ3) is assigned, and the gain of the R channel to which the first image signal P1 (λ1) is assigned are set to be higher in the order of B, G and R, bleeding and a mucous membrane are displayed in reddish color and blood vessels in a deep part are displayed in green color.

As described above, the above embodiment enables provision of the endoscope apparatus 1 that clearly displays relatively-thick blood vessels in a deep part of a mucous membrane using the first image signal P1 from among the three image signals from the image pickup device 2.

In other words, narrow-band light providing the above-described absorption characteristic between the maximal value and the minimal value of the absorption characteristic of a body tissue such as illustrated in FIG. 4 is irradiated to a mucous membrane of a living body, and an image of the resulting return light is displayed on a screen of the observation monitor 5 with relatively-thick blood vessels in a relatively-deep part of the mucous membrane of the living body enhanced. Accordingly, a surgeon can perform a desired treatment such as ESD while viewing relatively-thick blood vessels as well.

Also, if in the color conversion processing section 101b, using two or three image signals from among the first to third image signals P1, P2 and P3, channel assignment is performed for the first image signal P1, the second image signal P2 and the third image signal P3 and the image signals are outputted to the observation monitor 5, e.g., relatively-thick blood vessels and capillary vessels in a surface layer of a mucous membrane can be displayed.

In other words, in the above-described endoscope apparatus 1, blood vessels existing in a part close to a surface part of a mucous membrane of a living body can be displayed using the third narrow-band light NL3.

For example, since the third narrow-band light NL3 with wavelengths of around 540 nm is used, a state of capillary vessels in a surface part is displayed on the screen of the observation monitor 5 together with thick blood vessels. Furthermore, since the second narrow-band light NL2 with wavelengths of around 630 nm is used, a state of blood vessels in a deeper part is also displayed on the screen of the observation monitor 5.

Accordingly, a surgeon can use an endoscopic image on the screen of the observation monitor 5 not only for treatment, but also diagnosis of body tissues, for example, diagnosis for existence of cancer, area diagnosis for specifying an area of cancer and differential diagnosis for determining whether a diseased part is benign or malignant, from a state of capillary vessels, for example, the degree of concentration or dispersion of capillary vessels. Furthermore, e.g., penetration depth diagnosis taking blood vessels in a deeper part into consideration can also be performed.

Furthermore, the light-adjusting circuit 43 weighs the luminance values of the respective signals based on light adjustment parameters according to the observation mode to generate a light adjustment reference signal Y. In particular, in the narrow-band light observation mode, the light-adjusting circuit 43 provides a largest weight to the narrow-band light with wavelengths of around 600 nm to generate a light adjustment reference signal Yn. Then, since the light-adjusting circuit 43 controls the diaphragm in the diaphragm apparatus 13 so as to obtain proper image signals in the narrow-band light observation mode, an endoscopic image in the narrow-band light mode is clearly displayed with proper brightness without, e.g., saturation of any particular luminance value.

Although the above-described light source apparatus 4 generates illuminating light with a desired wavelength band using, e.g., the xenon lamp 11 and the rotating filter 14, in the endoscope apparatus 1, as indicated by dotted lines, the light source apparatus 4 may be configured so as to include a light emitting section 11A including a light emitting diode group 11a that includes a plurality of light emitting diodes (LED) that emit desired wavelengths, for example, respective RGB wavelengths corresponding to the first filter group and respective wavelengths of around 600 nm and around 630 nm corresponding to the second filter group. In such case, the light emitting section 11A and the light guide 15 provide an illumination section that irradiates illuminating light to an object.

For example, in FIG. 1, the light emitting section 11A, which is indicated by dotted lines, is provided in the light source apparatus 4 instead of, e.g., the xenon lamp 11, the heat-ray cut filter 12, the diaphragm apparatus 13 and the rotating filter 14. Furthermore, in the light source apparatus 4, a drive circuit 11b for driving the respective light emitting diodes in the light emitting section 11A at predetermined timings according to the respective modes is provided. The light emitting section 11A including the plurality of LEDs 11a receives power from the power supply 10 and is driven by the control of the drive circuit 11b according to a control signal from the control circuit 17.

Provision of the above-described endoscope apparatus 1 using such light source apparatus also enables provision of effects similar to the above-described effects.

Note that the light emitting section 11A may use a laser diode (LD) that emits a plurality of predetermined narrow-band lights.

Furthermore, regardless of a xenon light source, an LED or an LD being mounted in the light source apparatus and even if the CCD 2 is not a monochromatic image pickup device, but is provided with an RGB color filter or a complimentary color filter as wavelength band limiting means or a wavelength band limiting section that transmits the first narrow-band light NL1, effects similar to the above-described effects can be provided.

Furthermore, the second narrow-band light NL2 indicated in FIG. 4 may be light with a band of wavelengths longer than the wavelength for the minimal value ACmin in the absorption characteristic of hemoglobin (here, an absorption coefficient for a wavelength of 730 nm). In other words, for the wavelengths of the second narrow-band light NL2, use of, for example, 740 nm, 770 nm, 805 nm, 810 nm, 850 nm, 870 nm, 880 nm, 910 nm, 940 nm, 1020 nm or 1300 nm in a wavelength band providing an absorption coefficient lower than those of the wavelengths of the first narrow-band light NL1 and providing a suppressed scattering characteristic of a body tissue also enables provision of effects similar to the above-described effects (for example, if the narrow-band light NL2 is set to have any wavelengths of 740 to 1300 nm, the narrow-band light NL1 is set to have any of wavelengths of no less than 576 nm and at least no more than 630 nm). Note that, regardless of a xenon light source, an LED or an LD being mounted as a light source apparatus, the second narrow-band light NL2 can be generated.

As described above, the present embodiment enables provision of an endoscope apparatus capable of clearly displaying blood vessels in a deep part of a mucous membrane with proper brightness without troublesome work such as medical agent administration.

Second Embodiment

Although in the first embodiment, at least one narrow-band light including the first narrow-band light NL1 is actually irradiated to a body tissue as illuminating light and the above-described color conversion processing is performed on an image of return light of the narrow-band light, in the present embodiment, at least one narrow-band light is not actually irradiated to a body tissue and image information on an image of return light of each narrow-band light is obtained by what is called spectral estimation and color conversion processing is performed on spectral image signals with respective wavelengths obtained by the spectral estimation. In other words, although in the above-described first embodiment, the first narrow-band light NL1 is generated by an illumination apparatus including a rotating filter or a light emitting device such as a light emitting diode and color conversion processing is performed on an image of return light of the first narrow-band light NL1, in the present embodiment, an image signal for first narrow-band light NL1 is obtained by spectral estimation processing and color conversion processing is performed on an estimated spectral image signal obtained by the spectral estimation.

Figure 9:
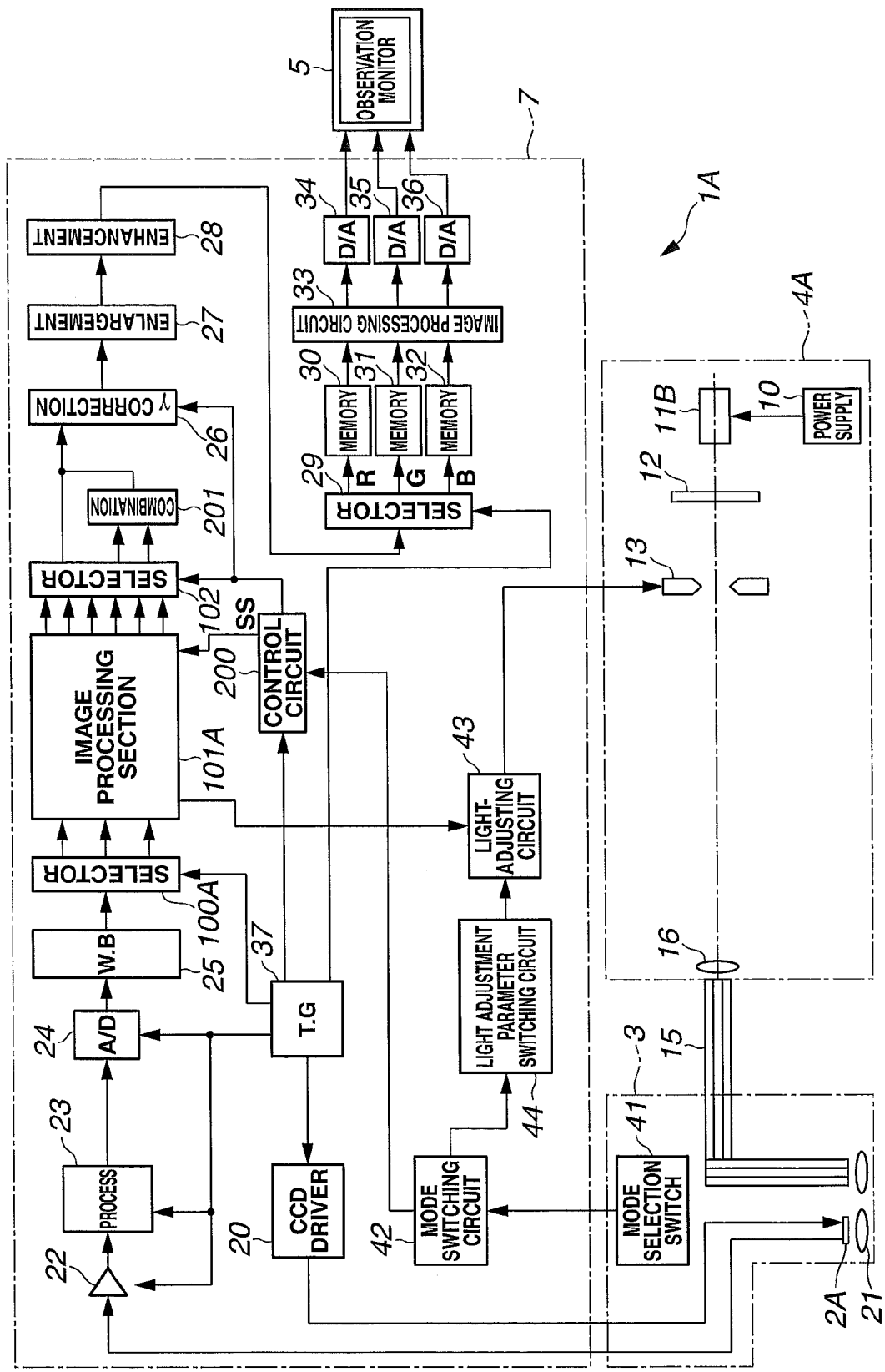
FIG. 9 is a configuration diagram illustrating a configuration of an endoscope apparatus 1A according to a second embodiment of the present invention.

FIG. 9 is a configuration diagram of a configuration of an endoscope apparatus 1A according to the second embodiment. In FIG. 9, components that are the same as those in FIG. 1 are provided with reference numeral that are the same as those in FIG. 1 and a description thereof will be omitted.

As illustrated in FIG. 9, a light source apparatus 4A includes a lamp 11B that emits white light, a heat-ray cut filter 12 and a diaphragm apparatus 13. Illuminating light from the light source apparatus 4A is irradiated to an object via a light guide 15. Note that the lamp 11B may be one that emits light other than white light.

An image pickup device 2A provided at a distal end of an insertion portion of an endoscope 3 is a color image pickup device. The image pickup device 2A is, for example, a color CCD, and includes an RGB color filter on an image pickup surface. Return light from the object is received by respective pixel sections of the image pickup surface via the RGB color filter, which is wavelength band limiting means or a wavelength band limiting section, and image signals of three colors, i.e., RGB, are outputted from the image pickup device 2A.

A selector 100A outputs the three image signals of RGB to an image processing section 101A. The image processing section 101A includes a spectral estimation section, and outputs an estimated spectral image signal with wavelengths of around 600 nm in a narrow-band light observation mode. Here, in the narrow-band light observation mode, the spectral estimation section in the image processing section 101A outputs three image signals, more specifically, an estimated spectral image signal with wavelengths of around 600 nm, an estimated spectral image signal with wavelengths of around 630 nm and an estimated spectral image signal with wavelengths of around 540 nm.

Figure 10:
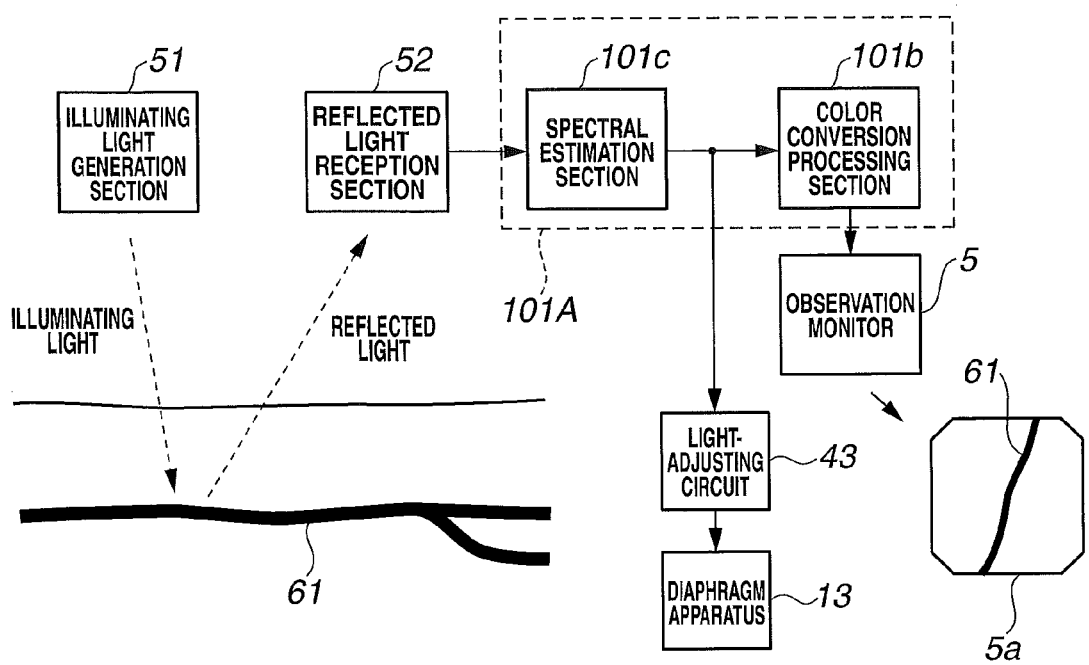
FIG. 10 is a diagram for describing an overall flow of processing in a narrow-band light observation according to the second embodiment of the present invention.

FIG. 10 is a diagram for describing the overall flow of processing in a narrow-band light observation according to the present embodiment. In FIG. 10, components that are the same as those in FIG. 3 are provided with reference numerals that are the same as those in FIG. 3 and a description thereof will be omitted. The image processing section 101A includes a spectral estimation section 101c in addition to a color conversion processing section 101b. In other words, the image processing section 101A provides image output means or an image output section that generates a first image signal by performing spectral estimation processing on an image pickup signal of return light and outputs the first image signal. Here, the spectral estimation section 101c extracts a first estimated spectral image signal e1 with wavelengths of around 600 nm, a second estimated spectral image signal e2 with wavelengths of around 630 nm and a third estimated spectral image signal e3 with wavelengths of around 540 nm from three images of RGB by spectral estimation processing and outputs the estimated spectral image signals to the color conversion processing section 101b.

More specifically, the spectral estimation section 101c calculates an n-dimensional spectral image by a matrix operation, based on a priori information provided in advance from three inputs, and selectively outputs e1, e2, e3 from among signals of the calculated n-dimensional estimated spectral image. The spectral estimation section 101c is configured to calculate an estimated spectral image signal e1 with wavelengths of around 600 nm, an estimated spectral image signal e2 with wavelengths of around 630 nm and an estimated spectral image signal e3 with wavelengths of around 540 nm using, e.g., a matrix operation and output the estimated spectral image signals.

Subsequent processing on the first, second and third estimated spectral image signals outputted from the spectral estimation section 101c in the color conversion processing section 101b is the same as the processing described in the first embodiment described above.

Also, the first, second and third estimated spectral image signals obtained by spectral estimation in the spectral estimation section 101c are inputted to a light-adjusting circuit 43.

Figure 11:
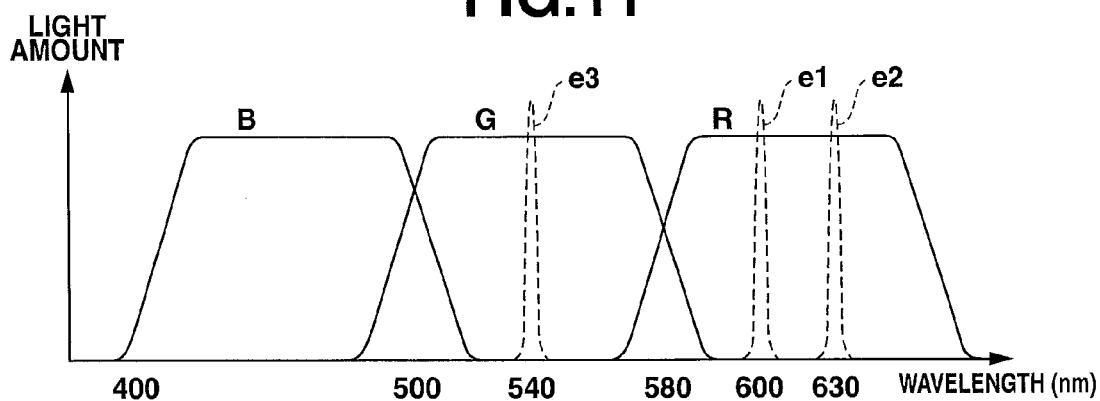
FIG. 11 is a diagram illustrating spectral characteristics for describing a case where spectral image signals e1, e2 and e3 of three narrow-band lights are estimated from image signals B, G and R of three wide-band lights, according to the second embodiment of the present invention.

FIG. 11 is a diagram indicating spectral characteristics for describing a case where spectral image signals e1, e2 and e3 of three narrow-band lights are estimated from image signals B, G and R of three wide-band lights. The wide-band lights B, G and R in FIG. 11 are obtained via the color filter in the image pickup device 2A, and image signals of three wide-band lights of B, G and R are inputted to the spectral estimation section 101c.

The spectral estimation section 101c estimates an estimated spectral image signal e1 of at least one narrow-band light from the image signals B, G and R of the three wide-band lights by spectral estimation processing. Here, an estimated spectral image signal e1 of narrow-band light with wavelengths of around 600 nm, an estimated spectral image signal e2 of narrow-band light with wavelengths of around 630 nm and an estimated spectral image signal e3 of narrow-band light with wavelengths of around 540 nm are obtained from image signals B, G and R of wide-band lights each having a wavelength band such as indicated in FIG. 11, by spectral estimation processing. Here, estimated spectral image signals e1 and e2 of two narrow-band lights in the wavelength band R between the maximal value ACmax and the minimal value ACmin in FIG. 4 and an estimated spectral image signal e3 for narrow-band light outside the wavelength band R are obtained by spectral estimation, and the estimated spectral image signals e1, e2 and e3 are supplied to the color conversion processing section 101b.

Also, one estimated spectral image signal e1 (here, three spectral image signals e1, e2 and e3) may be obtained from image signals of two wide-band lights from among the three wide-band lights, for example, image signals of the wide-band lights G and R, by spectral estimation processing.

Figure 12:
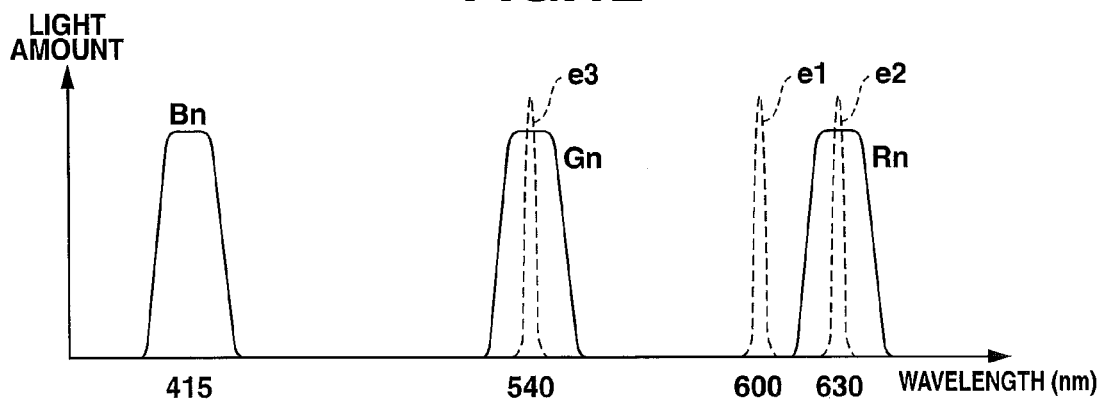
FIG. 12 is a diagram illustrating spectral characteristics for describing a case where estimated spectral image signals e1, e21 and e31 of three narrow-band lights are estimated from image signals of three narrow-band lights Bn, Gn and Rn, according to the second embodiment of the present invention.

Furthermore, an estimated spectral image signal e1 (here, three estimated spectral image signals e1, e2 and e3) may be obtained not from wide-band light such as indicated in FIG. 11 but from an image signal of narrow-band light such as indicated in FIG. 12, by spectral estimation processing.

FIG. 12 is a diagram illustrating spectral characteristics for describing a case where estimated spectral image signals e1, e21 and e31 of three narrow-band lights are estimated from image signals of three narrow-band lights Bn, Gn and Rn. As illustrated in FIG. 12, the spectral estimation section 101c estimates three estimated spectral image signals, that is, an estimated spectral image signal e1 of narrow-band light with wavelengths of around 600 nm, an estimated spectral image signal e2 of narrow-band light with wavelengths of around 630 nm and an estimated spectral image signal e3 of narrow-band light with wavelengths of around 540 nm from image signals Bn, Gn and Rn of three narrow-band lights.

Also, at least one estimated spectral image signal e1 may be obtained from at least one narrow-band light and at least one wide-band light, by spectral estimation. In other words, at least one of the three wide-band lights in FIG. 11 may be narrow-band light, or at least one of the three narrow-band lights in FIG. 12 may be wide-band light.

Also, three narrow-band lights Bn, Gn and Rn may be obtained via the color filter in the image pickup device 2A, the color filter having spectral characteristics such as indicated in FIG. 11 or FIG. 12, or it is possible to generate three narrow-band lights Bn, Gn and Rn using the rotating filter such as illustrated in FIG. 2 in the light source apparatus and apply return lights of three illuminating lights (that is, illuminating lights of three narrow-band lights Bn, Gn and Rn) to a monochromatic image pickup device.

Furthermore, image signals of three (or two) wide-band lights may be obtained not using a color filter in a color image pickup device, and it is possible to apply return lights of three (or two) illuminating lights, which are generated by arranging a first group of filters in a rotating filter, the filters having sensitivity characteristics that provide image signals such as indicated in FIG. 11 or FIG. 12, on an optical path in the light source apparatus, to a monochromatic image pickup device.

Accordingly, the endoscope apparatus 1A according to the present embodiment also enables provision of effects similar to the effects of the endoscope apparatus 1 described above.

As with the first embodiment, the light-adjusting circuit 43 generates a light adjustment reference signal Y according to the observation mode, and a light adjustment control parameter switching circuit 44 outputs light adjustment control parameters according to the mode to the light-adjusting circuit 43.

In the normal light observation mode, as with the first embodiment, the light-adjusting circuit 43 generates a light adjustment reference signal Yw based on three image pickup signals from a process circuit 23 and the light adjustment control parameters from the light adjustment control parameter switching circuit 44 using equation (1) above.

In the narrow-band light observation mode, the light-adjusting circuit 43 generates a light adjustment reference signal Yn1w based on equation (3) below.

$$Yn1 = 0.3 esIb(630) + 0.6 esIb(600) + 0.1 esIb(540) \quad \text{Equation (7)}$$

Here, esIb(630) is a luminance value of an estimated spectral image signal e2 of narrow-band light with wavelengths of around 630 nm, esIb(600) is a luminance value of an estimated spectral image signal e1 of narrow-band light with wavelengths of around 600 nm, and esIb(540) is a luminance value of an estimated spectral image signal e3 of narrow-band light with wavelengths of around 540 nm. Each luminance value is, for example, an average value of each luminance value for one frame. As indicated in equation (7), in the narrow-band light observation mode, the respective estimated spectral image signals e1, e2 and e3 are multiplied by respective light adjustment control parameters. Here, "0.6", which is a largest weight, is provided to the estimated spectral image signal e1 of the narrow-band light with wavelengths of around 600 nm.

Here, the values of the respective light adjustment control parameters in equation (7) are 0.6, 0.3 and 0.1, which are the same as those of equation (1), but may be different from those of equation (1).

Accordingly, in the narrow-band light observation mode, as with the first embodiment, the light-adjusting circuit 43 multiplies the image signal of the estimated spectral image signal e1 of the narrow-band light with wavelengths of around 600 nm, which is a most important signal, by a weight coefficient larger than those of the other image signals to generate a light adjustment reference signal Yn1, and controls a diaphragm in a diaphragm apparatus 13 based on the light adjustment reference signal Yn1.

In other words, the light-adjusting circuit 43 weighs the luminance values of the respective narrow-band lights based on the light adjustment parameters according to the observation mode to generate a light adjustment reference signal, and in particular, in the narrow-band light observation mode, provides a largest weight to the estimated spectral image signal e1 of the narrow-band light with wavelengths of around 600 nm to generate a light adjustment reference signal Yn1.

Figure 13:
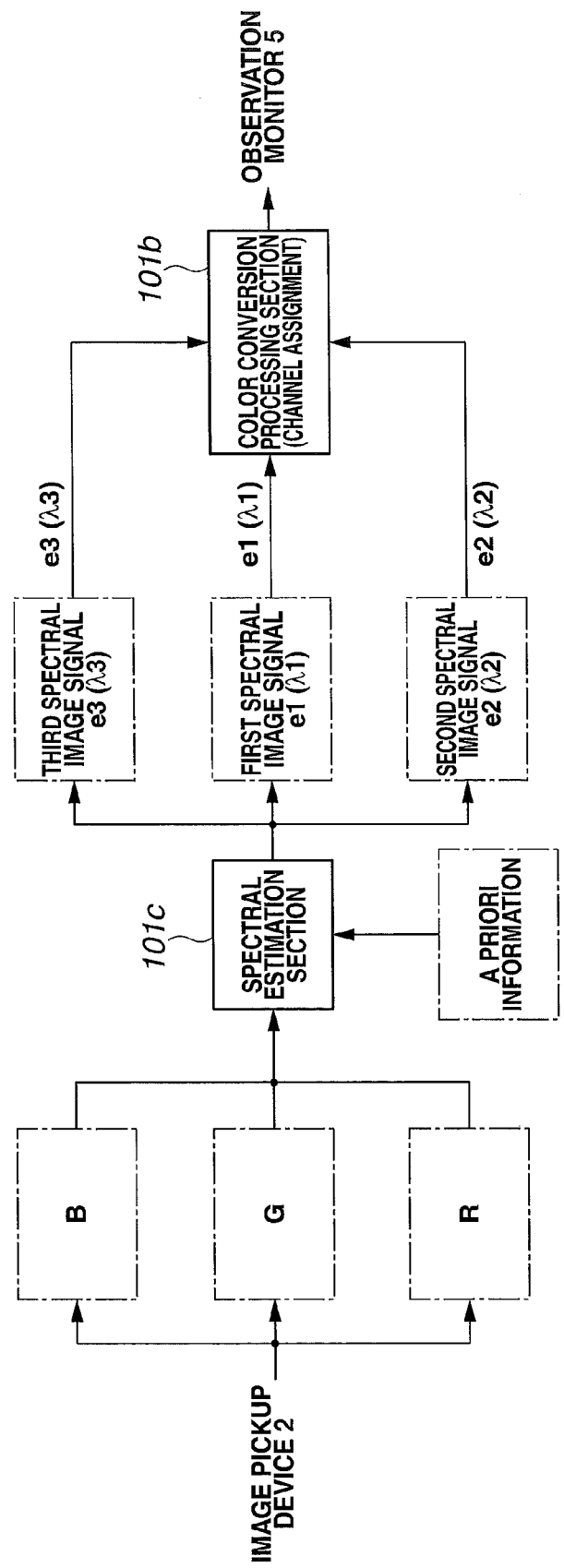
FIG. 13 is a diagram for describing a flow of processing on an image obtained from an image pickup device 2 in an image processing section 101A according to the first embodiment of the present invention.

FIG. 13 is a diagram for describing the flow of processing on an image obtained from the image pickup device 2 in the image processing section 101A according to the present embodiment.

As illustrated in FIG. 13, three images, that is, first to third image signals P1, P2 and P3 are inputted from the image pickup device 2 to the spectral estimation section 101c. The spectral estimation section 101c estimates three estimated spectral image signals e1, e2 and e3 from the inputted two or three image signals and thereby generates the estimated spectral image signals. In other words, a video processor 7 provides image signal processing means or an image signal processing section that generates a first image signal P1, a second image signal P2 and a third image signal P3 by performing spectral estimation processing on image pickup signals of return lights and outputs the image signals.

The color conversion processing section 101b performs color conversion processing on the first estimated spectral image signal e1, the second estimated spectral image signal e2 and the third estimated spectral image signal e3 by channel assignment and outputs the resulting signals to an observation monitor 5.

Although in the second embodiment, the color filter provided on the surface of the image pickup device has been described taking a RGB one as an example, the color filter may be a complimentary color filter.

With the endoscope according to the present embodiment, as a result of the above-described color conversion processing being performed, relatively-thick blood vessels in a relatively-deep part of a mucous membrane of a living body are clearly displayed on a screen of the observation monitor 5. Accordingly, a surgeon can perform a desired treatment such as ESD while viewing relatively-thick blood vessels as well.

Furthermore, since the above-described endoscope apparatus 1A is capable of displaying blood vessels existing in a part close to a surface layer of a mucous membrane of a living body using the third estimated spectral image signal e3, the endoscope apparatus 1A can be used also for diagnosis of body tissues, for example, diagnosis for existence of cancer, area diagnosis for specifying an area of cancer and differential diagnosis for determining whether a diseased part is benign or malignant, from a state of capillary vessels, for example, the degree of concentration or dispersion of capillary vessels. Furthermore, e.g., penetration depth diagnosis taking blood vessels in a deeper part into consideration can also be performed.

Also, it is possible to perform color conversion processing using fourth and fifth images obtained by further spectral estimation in addition to the third estimated spectral image signal e3, and display the resulting image on the observation monitor 5.

Furthermore, the light-adjusting circuit 43 provides a weight to each of luminance values of respective estimated spectral image signals based on light adjustment parameters according to the observation mode to generate a light adjustment reference signal, and in particular, in the narrow-band light observation mode, provides a largest weight to the estimated spectral image signal e1 of the narrow-band light with wavelengths of around 600 nm to generate a light adjustment reference signal Yn1. Then, since the light-adjusting circuit 43 controls the diaphragm in the diaphragm apparatus 13 so as to obtain image signals with proper brightness in the narrow-band light observation mode, an endoscopic image in the narrow-band light mode is clearly displayed with proper brightness without, e.g., saturation of any particular luminance value.

Also, a peak wavelength of the second estimated spectral image signal e2 indicated in FIG. 11 or FIG. 12 may be light with a band of wavelengths that are longer than the wavelength for the minimal value ACmin (here, the absorption coefficient for a wavelength of 730 nm) in the absorption characteristic of hemoglobin in FIG. 4. In other words, use of a wavelength band that provides an absorption coefficient lower than that of a peak wavelength of the first estimated spectral image signal e1 and provides a suppressed scattering characteristic of a body tissue, for example, 740 nm, 770 nm, 805 nm, 810 nm, 850 nm, 870 nm, 880 nm, 910 nm, 940 nm, 1020 nm or 1300 nm, for the peak wavelength of the second estimated spectral image signal e2 enables provision of effects equivalent to the above-described effects (for example, if the peak wavelength of the second estimated spectral image signal e2 is set to a wavelength in a range of 740 to 1300 nm, a wavelength in a range of no less than 576 nm and at least no more than 630 nm is set as the peak wavelength of the first estimated spectral image signal e1).

As described above, the above-described present embodiment enables provision of an endoscope apparatus capable of clearly displaying blood vessels in a deep part of a mucous membrane with proper brightness without troublesome work such as medical agent administration.

Third Embodiment

In the first embodiment, at least one narrow-band light including the first narrow-band light NL1 is actually irradiated to a body tissue as illuminating light and the above-described color conversion processing is performed on an image of the return light, and in the second embodiment, at least one narrow-band light including the first narrow-band light NL1 is not actually irradiated to a body tissue but image information on return lights of the respective narrow-band lights is obtained by what is called spectral estimation and the above-described color conversion processing is performed on the estimated spectral image signals of the respective wavelengths obtained by the spectral estimation; however, in a third embodiment, the above-described color conversion processing is performed on an image signal of return light of actual illuminating light of narrow-band light and an estimated spectral image signal obtained by spectral estimation.

Figure 14:
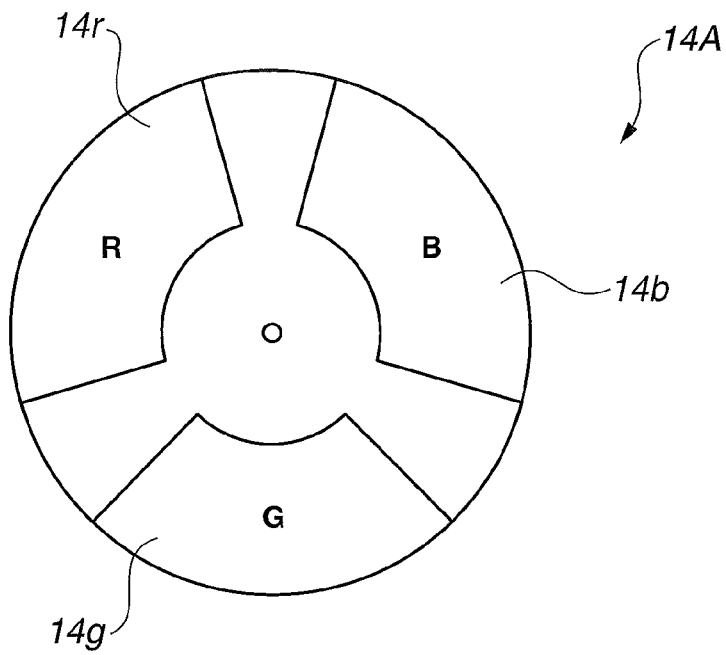
FIG. 14 is a diagram illustrating a configuration of a rotating filter 14A according to a third embodiment of the present invention.

Although a configuration of an endoscope apparatus 1B according to the present embodiment is the same as the configuration of the endoscope apparatus 1 illustrated in FIG. 1, a configuration of a rotating filter 14A in the present embodiment is different from that in FIG. 1. FIG. 14 is a diagram illustrating a configuration of a rotating filter 14A according to the present embodiment. As illustrated in FIG. 14, the rotating filter 14A only includes an RGB filter section that provides a filter set for outputting frame-sequential light with spectral characteristics for normal light observation. Return light of the frame-sequential BGR light is received by a monochromatic image pickup device 2.

Furthermore, as indicated by an alternate long and two short dashes line, the endoscope apparatus 1B according to the present embodiment is different from the configuration of the endoscope apparatus 1 according to the first embodiment and is the same as the endoscope apparatus 1A according to the second embodiment in that an estimated spectral image signal is inputted from the image processing section 101B to a light-adjusting circuit 43.

Figure 15:
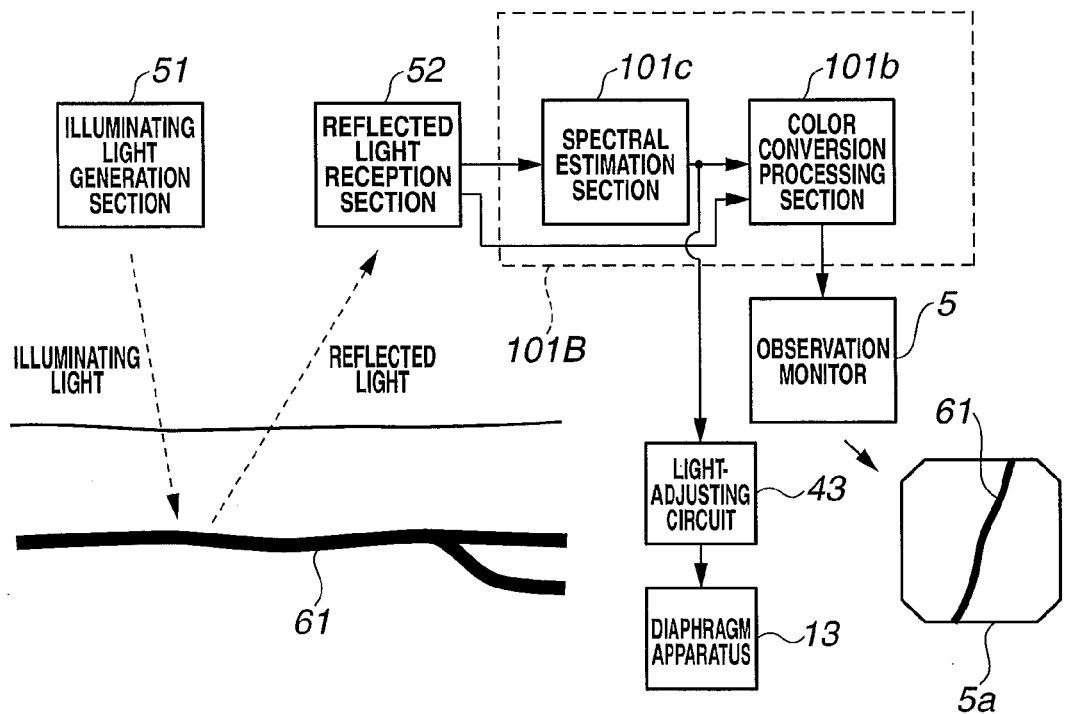
FIG. 15 is a diagram for describing an overall flow of processing in a special-light observation mode according to the third embodiment of the present invention.

FIG. 15 is a diagram for describing the overall flow of processing in a special-light observation mode according to the present embodiment. In FIG. 15, components that are the same as those in FIG. 10 are provided with reference numerals that are the same as those in FIG. 10 and a description thereof will be omitted. The image processing section 101B includes a color conversion processing section 101b and a spectral estimation section 101c, and the spectral estimation section 101c generates at least one estimated spectral image signal e from two or three image signals from among RGB and color conversion processing is performed on one image signal from among RGB and the estimated spectral image signal.

Here, more specifically, a first estimated spectral image signal e1 with wavelengths of around 600 nm and a third estimated spectral image signal e3 with wavelengths of around 540 nm are estimated from three (or two) image signals from among RGB by spectral estimation processing and outputted to the color conversion section 101b.

In FIG. 15, in a normal light observation mode, as with the first embodiment, the light-adjusting circuit 43 generates a light adjustment reference signal Y based on three image pickup signals from a process circuit 23 and light adjustment control parameters from a light adjustment control parameter switching circuit 44 using equation (1) above. In a special-light observation mode, the light-adjusting circuit 43 generates a light adjustment reference signal Yn2 based on equation (8) below.

$$Yn2 = 0.3Ib(R) + 0.6esIb(600) + 0.1esIb(540) \qquad \text{Equation (8)}$$

Here, Ib(R) is a luminance value of an R signal, esIb(600) is a luminance value of an estimated spectral image signal e1 of narrow-band light with wavelengths of around 600 nm, esIb(540) is a luminance value of an estimated spectral image signal e3 of narrow-band light with wavelengths of around 540 nm. Each luminance value is, for example, an average value of each luminance value for one frame. As indicated in equation (8), in the special-light observation mode, the respective estimated spectral image signals e1 and e3 and the R signal are multiplied by respective light adjustment control parameters. Here, "0.6", which is a largest weight, is provided to the estimated spectral image signal e1 of the narrow-band light with wavelengths of around 600 nm.

Here, the values of the respective light adjustment control parameters in equation (8) are 0.6, 0.3 and 0.1, which are the same as those of equation (1), but may be different from those of equation (1).

Accordingly, in the special-light observation mode, as with the second embodiment, the light-adjusting circuit 43 multiplies the image signal of the estimated spectral image signal e1 of the narrow-band light with wavelengths of around 600 nm, which is a most important signal, by a weight coefficient larger than those of the other image signals to generate a light adjustment reference signal Yn2, and controls a diaphragm in a diaphragm apparatus 13 based on the light adjustment reference signal Yn2.

In other words, the light-adjusting circuit 43 weighs the luminance values of the respective narrow-band lights based on the light adjustment parameters according to the observation mode to generate a light adjustment reference signal, and in particular, in the special-light observation mode, provides a largest weight to the estimated spectral image signal e1 of the narrow-band light with wavelengths of around 600 nm to generate a light adjustment reference signal Yn2.

Figure 16:
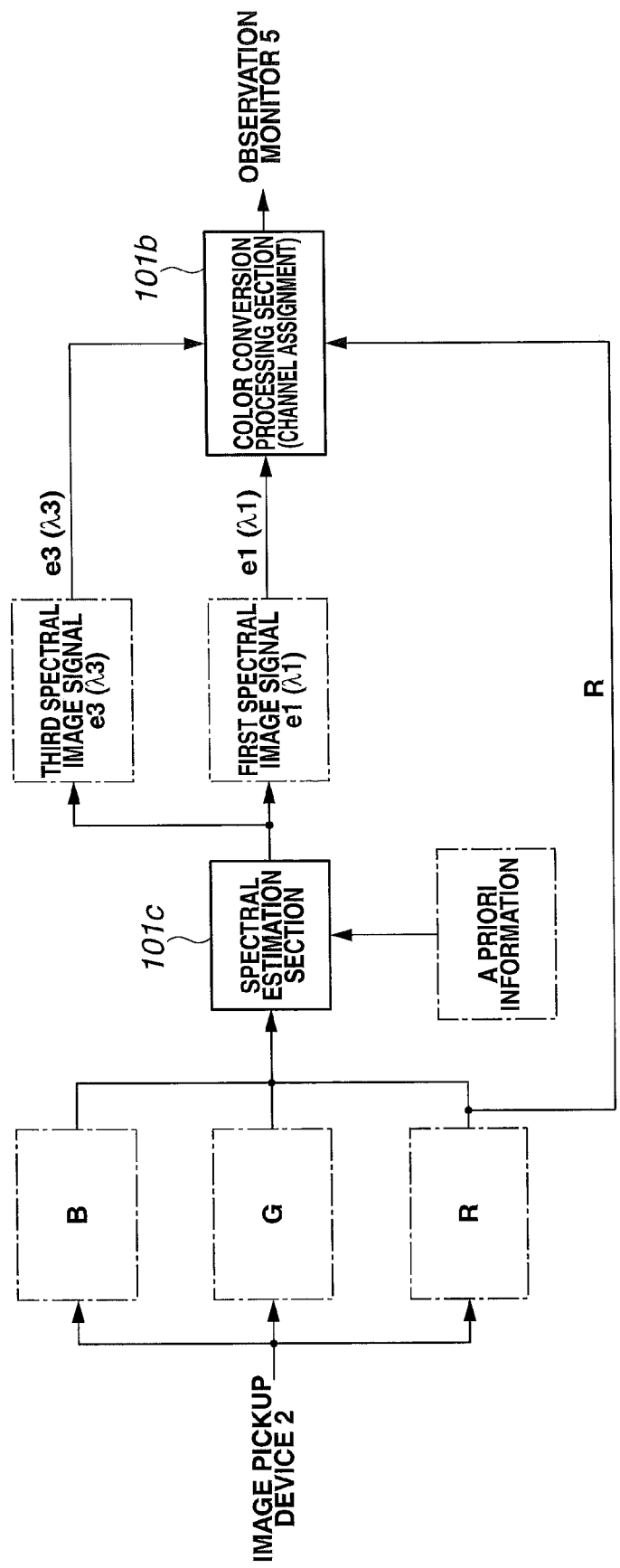
FIG. 16 is a diagram for describing a flow of processing on an image obtained from an image pickup device 2 in an image processing section 101B according to the third embodiment of the present invention.

FIG. 16 is a diagram for describing the flow of processing on an image obtained from the image pickup device 2 in the image processing section 101B according to the present embodiment.

As illustrated in FIG. 16, three images, that is, first to third image signals B, G and R, are inputted from the image pickup device 2 to the spectral estimation section 101c. The spectral estimation section 101c estimates two estimated spectral image signals e1 and e3 from the inputted two or three images and thereby generates the estimated spectral image signals.

The color conversion processing section 101b performs color conversion processing on the estimated spectral image signal e1, the estimated spectral image signal e3 and the image signal R by channel assignment and outputs the resulting signals to an observation monitor 5.

Note that the processing in the color conversion processing section 101b is the same as that of the first embodiment.

Figure 17:
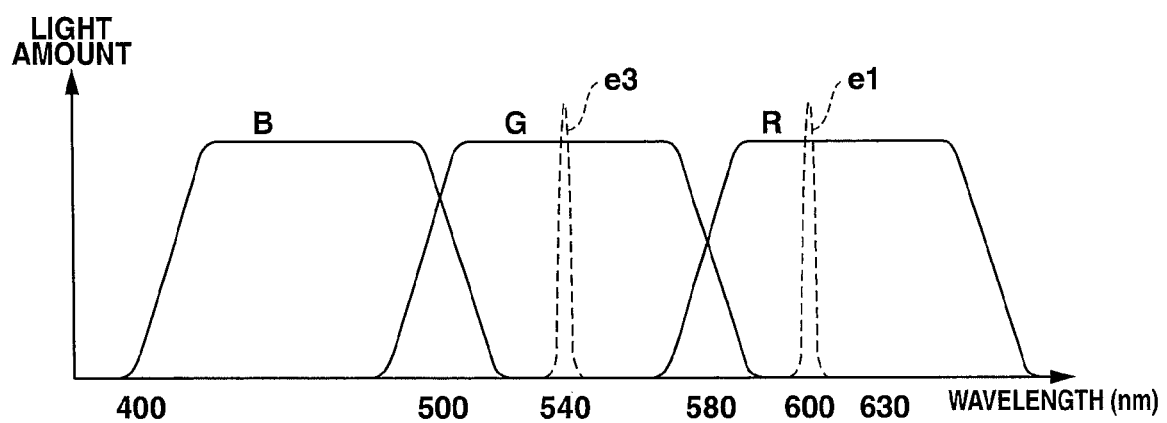
FIG. 17 is a diagram illustrating spectral characteristics for describing a case where an estimated spectral image signal e1 of at least one narrow-band light is estimated from image signals B, G and R of three (or two) wide-band lights, according to the third embodiment of the present invention.

FIG. 17 is a diagram illustrating spectral characteristics for describing a case where an estimated spectral image signal e1 of at least one narrow-band light is estimated from image signals B, G and R of three (or two) wide-band lights. Here, estimated spectral image signals e1 and e3 of two narrow-band lights are estimated from image signals B, G and R of three wide-band lights.

As illustrated in FIG. 16, the spectral estimation section 101c generates spectral image signals e1 and e3 by spectral estimation using signal processing based on at least two image pickup signals (here, three image pickup signals B, G and R) of return lights from a subject and outputs the spectral image signals e1 and e3.

The estimated spectral image signals e1 and e3 outputted from the spectral estimation section 101c and a realistic image signal R are inputted to the color conversion processing section 101b. As described above, processing in the color conversion processing section 101b is the same as the processing described in the first embodiment described above.

Accordingly, if color conversion processing is performed so that only the spectral image signal e1 obtained by spectral estimation is monochromatically displayed as described above, thick blood vessels 61 below a mucous membrane can clearly be displayed, and if color conversion processing is performed so that at least one of the other two image signals, that is, the spectral image signal e3 and the realistic image signal R is included and displayed in addition to the spectral image signal e1, not only thick blood vessels 61 below a mucous membrane, but also capillary vessels at a surface layer, and thick blood vessels in a deeper part can be displayed on the observation monitor 5.

Although in the above-described example, the third image signal with wavelengths of around 540 nm is obtained by spectral estimation, it is possible to obtain the second image signal with wavelengths of around 630 nm by spectral estimation and use the image signal B as a realistic image.

Furthermore, illuminating light for obtaining a realistic image signal may be narrow-band light illustrated in FIG. 12.

Furthermore, the three wide-band lights B, G and R in FIG. 16 may be obtained by a color filter in an image pickup device 2A. In other words, the three wide-band lights B, G and R may be obtained using a light source apparatus 4A and a color filter in an image pickup device 2A such as described in the second embodiment.

Accordingly, the endoscope apparatus 1B according to the present embodiment also enables provision of effects similar to the effects of the endoscope apparatuses 1 and 1A described above.

Although in the third embodiment, the description of the case where a color filter provided on a surface of the image pickup device is used is provided taking a RGB color one as an example, the color filter may be a complimentary color filter.

With the endoscope according to the present embodiment, as a result of the above-described processing being performed, relatively-thick blood vessels in a relatively-deep part of a mucous membrane of a living body are clearly displayed on a screen of the observation monitor 5. Accordingly, a surgeon can perform a desired treatment such as ESD while viewing relatively-thick blood vessels as well.

Also, since the above-described endoscope apparatus 1A is capable of displaying blood vessels existing in a part close to a surface layer of a mucous membrane of a living body using the estimated spectral image signal e3 for the third narrow-band light NL3 or narrow-band light Gn, the endoscope apparatus can be used also for diagnosis of body tissues, for example, diagnosis for existence of cancer, area diagnosis for specifying an area of cancer and differential diagnosis for determining whether a diseased part is benign or malignant, from a state of capillary vessels, for example, the degree of concentration or dispersion of capillary vessels. Furthermore, e.g., penetration depth diagnosis taking blood vessels in a deeper part into consideration can also be performed.

Furthermore, the light-adjusting circuit 43 provides a weight to luminance values of respective estimated spectral image signals based on light adjustment parameters according to the observation mode to generate a light adjustment reference signal, and in particular, in the special-light observation mode, provides a largest weight to the estimated spectral image signal e1 of the narrow-band light with wavelengths of around 600 nm to generate a light adjustment reference signal Yn2. Then, since the light-adjusting circuit 43 controls a diaphragm in a diaphragm apparatus 13 so as to obtain proper image signals in the special-light observation mode, an endoscopic image in the special-light observation mode is clearly displayed with proper brightness without, e.g., saturation of any particular luminance value.

Also, a center wavelength of each of the realistic image signals illustrated in FIG. 17 may be light with a band of wavelengths longer than the wavelength for the minimal value ACmin in the absorption characteristic of hemoglobin in FIG. 4 (here, the absorption coefficient for a wavelength of 730 nm). In other words, for a center wavelength of the realistic image signal, use of, for example, 740 nm, 770 nm, 805 nm, 810 nm, 850 nm, 870 nm, 880 nm, 910 nm, 940 nm, 1020 nm or 1300 nm in a wavelength band that provides an absorption coefficient lower than that of a peak wavelength of the first estimated spectral image signal e1 and provides a suppressed scattering characteristic of a body tissue enables provision of effects similar to the above-described effects (for example, if the wavelength of the realistic image signal is set to have any wavelengths of from 740 to 1300 nm, the peak wavelength of the first estimated spectral image signal e1 is set to have any wavelengths of no less than 576 nm and at least no more than 630 nm).

As described above, the present embodiment enables provision of an endoscope apparatus capable of clearly displaying blood vessels in a deep part of a mucous membrane with proper brightness without troublesome work such as medical agent administration.

(Modifications Common to Respective Embodiments)
(Modification 1)

Although in the above-described three embodiments and each modification of the respective embodiments, a light absorption characteristic of venous blood is taken as an example and two narrow-band lights are selected based on the characteristic, at least two narrow-band lights such as described above may be selected based on a light absorption characteristic of arterial blood or a light absorption characteristic of blood resulting from combining light absorption characteristics of both venous blood and arterial blood.

(Modification 2)

Although in the endoscope apparatus according to each of the above-described embodiments and each of the modifications (including the modifications of each embodiment), light with wavelengths of around 600 nm and light with wavelengths of 630 nm are used as wavelengths of the first narrow-band light NL1 and the second narrow-band light NL2, respectively, for the wavelengths of the first narrow-band light NL1 and the second narrow-band light NL2, narrow-band light with wavelengths in a range of wavelengths of 580 to 620 nm and having a distribution in a predetermined width range and narrow-band light with wavelengths in a range of wavelengths of 610 to 730 nm and having a distribution in a predetermined width range are preferable, respectively, and narrow-band light with wavelengths in a range of wavelengths of 585 to 615 nm and having a distribution in a predetermined width range and narrow-band light with wavelengths in a range of wavelengths of 620 to 640 nm and having a distribution in a predetermined width range are more preferable, respectively.

Accordingly, wavelengths of the first narrow-band light NL1 and the second narrow-band light NL2 are not limited to light with wavelengths of around 600 nm and light with wavelengths of around 630 nm, respectively, and may be light with any wavelengths as long as the lights are lights with wavelengths providing an absorption characteristic such as described above between a maximal value and a minimal value in the absorption characteristic. For example, for the wavelengths of the first narrow-band light NL1 and the second narrow-band light NL2, light with wavelengths of around 610 nm and light with wavelengths of around 645 nm or light with wavelengths of around 630 nm and light with wavelengths of around 660 nm may be used, respectively. Also, the first narrow-band light NL1 may have a spectral characteristic with a broad wavelength band.

(Modification 3)

Although in the endoscope apparatus according to each of the above-described embodiments and each of the modifications (including the modifications of each embodiment), light with wavelengths of around 540 nm is used as the third narrow-band light NL3 in order to display capillary vessels in a surface layer of a body tissue, the wavelengths of the third narrow-band light NL3 are not limited to these. For example, for the wavelengths of the third narrow-band light NL3, light with wavelengths of around 400 nm, which is shorter than a wavelength of 540 nm, may be used. In particular, in order to obtain information on a surface layer of a body tissue, light with wavelengths of around 460 nm and light with wavelengths of around 415 nm, which are shorter than a wavelength of 540 nm, may be employed. In particular, in order to obtain information on a surface layer of a body tissue, light with wavelengths of around 415 nm and light with wavelengths of 460 nm, which are shorter than a wavelength of around 540 nm, are desirable.

(Modification 4)

Although it has been described that for the light source apparatus according to each of the above-described embodiments and each of the modifications (including the modifications of each embodiment), e.g., a lamp with a heat light source, an LED or an LD is used, another means may be used. For example, for light source means or a light source section, a wavelength-variable laser may be used, or it is possible to excite a phosphor by an LED or an LD to generate broadband light and use the light.

(Modification 5)

In the endoscope apparatus according to each of the above-described embodiments and each of the modifications (including the modifications of each embodiment), if narrow-band light is irradiated, it is possible to, for example, generate narrow-band light with wavelengths of around 600 nm by a laser and generate narrow-band light with wavelengths of around 630 nm by an LED. Use of laser light enables reduction of noise in a depth direction. Also, it is possible to generate narrow-band light with wavelengths of around 600 nm by an LED and generate narrow-band light with wavelengths of around 630 nm by a laser.

(Modification 6)

Although in each of the above-described embodiments and each of the modifications (including the modifications of each embodiment), relatively-thick blood vessels in a deep part of a mucous membrane is clearly displayed by an image of narrow-band light with wavelengths of around 600 nm, an image of narrow-band light with longer wavelengths may be used in order to clearly display blood vessels in a deeper part. Then, in such case, display is provided on an observation monitor 5 using the above-described combination of wavelengths of around 600 nm and wavelengths of around 630 nm, but the other combinations may be provided in advance so that a surgeon can select a desired combination from among the plurality of combinations.

The endoscope apparatus 1 (or 1A or 1B) may be configured so as to have a first combination of a first image signal NL1 with wavelengths of around 600 nm and a second image signal NL2 with wavelengths of around 630 nm and a second combination of a first image signal NL12 with wavelengths of around 650 nm and a second image signal NL22 with wavelengths of around 680 nm as combinations of two display images so that a surgeon can select a desired combination from the two combinations.

With such configuration, as a result of a surgeon selecting a combination, the surgeon can perform observation with the depth of blood vessels changed to clearly display blood vessels in a desired depth together with blood vessels in a part deeper than those provided by the second image signal.

Figure 18:
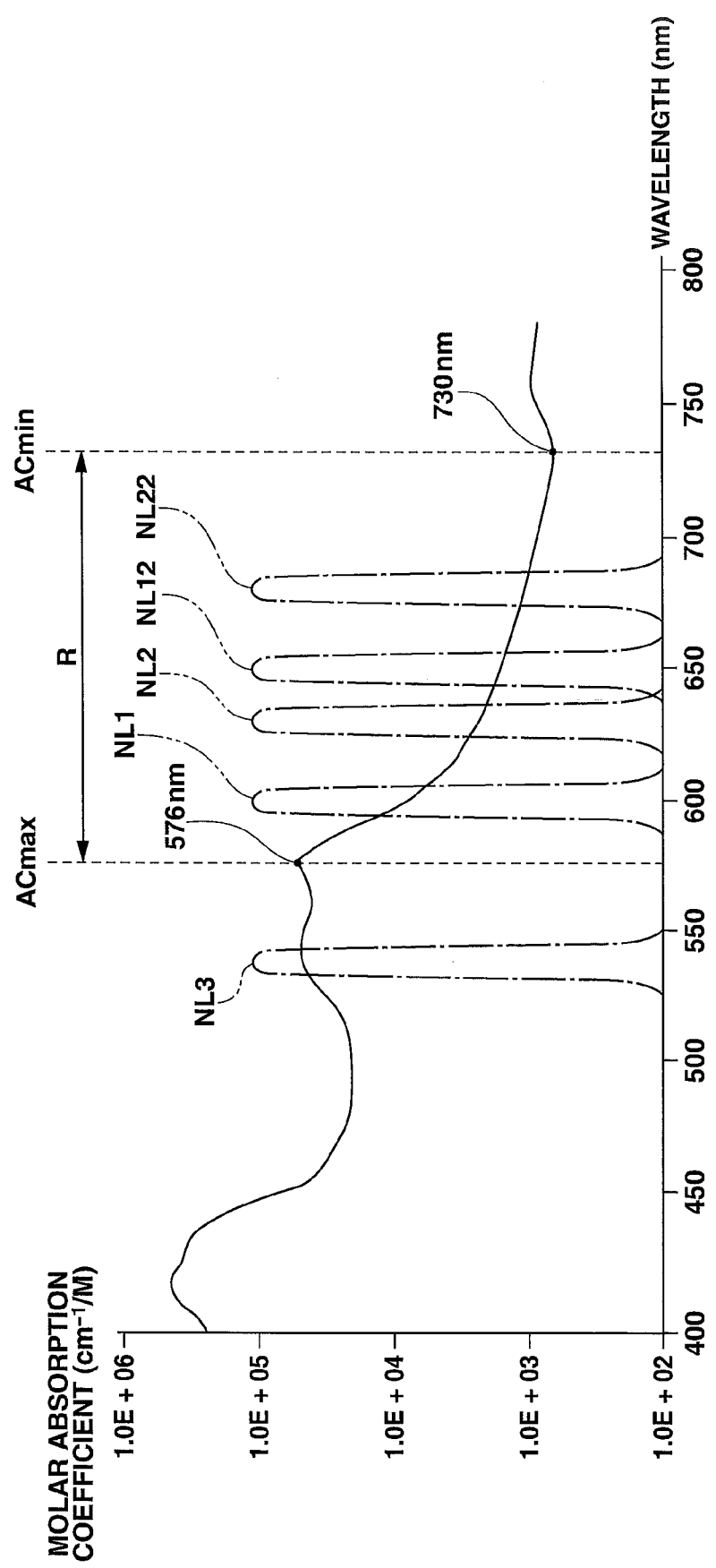
FIG. 18 is a diagram illustrating a light absorption characteristic of venous blood for describing modification 6.

FIG. 18 is a diagram illustrating light absorption characteristics of venous blood for describing modification 6. In FIG. 18, one of two combinations is a first combination of narrow-band light NL1 with wavelengths of around 600 nm and narrow-band light NL2 with wavelengths of around 630 nm and the other is a second combination of narrow-band light NL12 with wavelengths of around 650 nm and narrow-band light NL22 with wavelengths of around 680 nm. Which combination to select can be determined by a user: for example, a user can select which combination is used for performing display, by mode selection.

Also, the other combination may be any of, e.g., a combination of narrow-band light with wavelengths of around 615 nm and narrow-band light with wavelengths of around 645 nm and a combination of narrow-band light with wavelengths of around 630 nm and narrow-band light with wavelengths of around 660 nm.

Since in the case of the second combination, the used wavelengths are ones shifted to the long wavelength side compared to those of the first combination, an image of a deeper part is clearly displayed. Accordingly, where a surgeon wishes to display blood vessels in a deeper part, if, e.g., blood, bile or urine adheres to a surface of a mucous membrane of a living body, blood vessels in a desired depth can clearly be displayed by selecting the second combination.

It is preferable that a difference in wavelength between the two wavelength bands in each of the combinations is substantially the same in order to obtain contrasts similar to one another.

Two or more combinations may be provided by increasing the number of rotating filter combinations in the light source apparatus or the number of estimated spectral image signals estimated by spectral estimation processing.

For narrow-band light wavelength combinations, in order to clearly display blood vessels that are relatively shallow from a surface of a mucous membrane, it is preferable to provide two combinations that are a combination of wavelengths of around 580 nm and wavelengths of around 630 nm and a combination of wavelengths of around 590 nm and wavelengths of around 630 nm.

Furthermore, for narrow-band light wavelength combinations, in order to clearly display blood vessels in a deeper part from a surface of a mucous membrane or blood vessels below a mucous membrane below, e.g., blood, it is preferable to provide two combinations that are a combination of wavelengths of around 600 nm and wavelengths of around 630 nm and a combination of wavelengths of around 650 nm and wavelengths of around 680 nm.

Although in the above-described example, two combinations are provided, three or more combinations may be employed. In the case of three combinations, for example, a first combination of narrow-band light with wavelengths of around 600 nm and narrow-band light with wavelengths of around 630 nm, a second combination of narrow-band light with wavelengths of around 650 nm and narrow-band light with wavelengths of around 680 nm and a third combination of narrow-band light with wavelengths of around 700 nm and narrow-band light with wavelengths of around 730 nm.

As described above, since a plurality of display results can be provided, a surgeon can make desired blood vessels be clearly displayed by selecting a combination on the longer wavelength side (for example, a combination of wavelengths of around 650 nm and wavelengths of around 680 nm) when a concentration of, e.g., blood adhering to a surface of the mucous membrane of the living body is high, or furthermore, where the blood vessels exist in a relatively-shallow part, selecting a combination on the shorter wavelength side (for example, a combination of wavelengths of around 580 nm and wavelengths of around 630 nm) when the concentration of, e.g., blood adhering to the surface of the mucous membrane of the living body is low.

(Modification 7)

Although in each of the above-described embodiments and each of the modifications (including the modifications of each embodiment), a difference in wavelength between the two narrow-band lights that are the first image signal NL1 and the second image signal NL2 is fixed, it is possible that one of the wavelength bands is fixed and the other is variable.

For example, in the case of narrow-band light with wavelengths of around 600 nm and narrow-band light with wavelengths of around 630 nm, it is possible that the wavelength band of the narrow-band light with wavelengths of around 600 nm is fixed and the other narrow-band light is arbitrarily set to have any of variable wavelengths of around 630 nm to around 730 nm. Alternatively, it is possible that the wavelength band of the other narrow-band light with wavelengths of around 730 nm is fixed and narrow-band light with any of variable wavelengths of around 590 nm to around 620 nm is arbitrarily set. Also, it is possible that the wavelength band of the narrow-band light of around 600 nm is fixed and the other narrow-band light is arbitrarily set to have a wavelength band of no less than 730 nm.

As described above, for a difference in wavelength between two narrow-band lights, the wavelength band of one of the narrow-band lights is fixed and the wavelength band of the other is made to be variable, enabling blood vessels in a desired region to be clearly displayed.

(Modification 8)

Although in each of the above-described embodiments and each of the modifications (including the modifications of each embodiment), three images are obtained to display narrow-band images on the observation monitor 5, it is possible to further obtain a fourth image and generate a display image by arbitrarily selecting images from the four images.

An endoscope apparatus has a narrow-band observation mode in addition to a normal light observation mode, and a surgeon switches the observation mode from the normal light observation mode to the narrow-band light observation mode as necessary to perform various treatments. Addition of the fourth image enables a display image in each observation mode to be obtained easily.

For example, the fourth image is obtained using a light source apparatus capable of further irradiating illuminating light that is blue narrow-band light (or wide-band light) with wavelengths shorter than a wavelength of 540 nm. The light source apparatus alternately irradiates illuminating light with a first combination of light with the fourth wavelengths and narrow-band light with wavelengths of around 600 nm and a second combination of narrow-band light with wavelengths of around 540 nm and narrow-band light with wavelengths of around 630 nm to an object. Also, it is possible to alternately irradiate illuminating light with a combination of light with the fourth wavelengths and narrow-band light with wavelengths of around 540 nm and narrow-band light of wavelengths of around 600 nm and illuminating light of narrow-band light with wavelengths of around 630 nm to an object.

Furthermore, return lights of the respective illuminating lights are received by an image pickup device including an RGB color filter. For example, an image of the return light with the fourth wavelengths is picked up via a B-band region of the color filter and an image of the return light of the narrow-band light with wavelengths of around 600 nm is picked up via an R-band region. Also, the color filter of the image pickup device may be a complimentary color one. Furthermore, the image pickup device may be a monochromatic image pickup device.

Since images with the respective bands are separated from one another, four monochromatic images are obtained in a video processor 7. Note that, in order to obtain the respective images, proper color balance adjustment is performed on image signals of the respective lights.

Then, in the video processor 7, a normal image for a normal light observation mode is generated using images of four return lights of the light with the fourth wavelengths, the narrow-band light with wavelengths of around 540 nm, the narrow-band light with wavelengths of around 600 nm and the narrow-band light with wavelengths of around 630 nm.

Also, in the video processor 7, a first narrow-band light image is generated using two images of the light with the fourth wavelengths and the narrow-band light with wavelengths of around 540 nm by assigning the image signal of the light with the fourth wavelengths to B and G channels and assigning the image signal of the narrow-band light with wavelengths of around 540 nm to a R channel.

Furthermore, in the video processor 7, a second narrow-band light image is generated using three images of the narrow-band light with wavelengths of around 540 nm, the narrow-band light with wavelengths of around 600 nm and the narrow-band light with wavelengths of around 630 nm.

Note that the image signal of the narrow-band light with wavelengths of around 600 nm is displayed with high contrast.

Then, any of the images generated as described above is selected according to an image display instruction from a surgeon and displayed on an observation monitor 5.

Such configuration enables simultaneous display of a normal image for normal light observation and a narrow-band light image for narrow-band light observation and overlapping display of a normal image and a narrow-band light image. For example, parallel display of the normal light image and the first narrow-band light image (or the second narrow-band light image) or parallel display of the first narrow-band light image and the second narrow-band light image can be provided.

Furthermore, it is possible to generate an overlapping image with information on blood in a deep part added to a normal image by assigning the image signal of the light with the fourth wavelengths to the B channel, the image signal of the narrow-band light with wavelengths of around 540 nm to the G channel and the image signal of the narrow-band light with wavelengths of around 600 nm to the R channel, or assigning the image signal of the light with the fourth wavelengths to the B channel, the image signal of the narrow-band light with wavelengths of around 540 nm and the image signal of the narrow-band light with wavelengths of around 600 nm to the G channel, and the image signal of the narrow-band light with wavelengths of around 600 nm (or the image signal of the narrow-band light with wavelengths of around 600 nm and the image signal of the narrow-band light with wavelengths of around 630 nm) to the R channel, and display the overlapping image on the observation monitor 5.

Alternatively, it is possible to generate an image with blood vessels in both a surface layer and a deep part appearing with high contrast by assigning the image signal of the light with the fourth wavelengths to the B channel, the image signal with the fourth wavelengths and the image signal of the narrow-band light with wavelengths of around 600 nm to the G channel, the image signal of the narrow-band light with wavelengths of around 600 nm (or the image signal of the narrow-band light with wavelengths of around 600 nm and the image signal of the narrow-band light with wavelengths of around 630 nm) to the R channel, and display the image on the observation monitor 5.

Note that the image signal with the fourth wavelengths may be generated by spectral estimation.

As described above, modification 8 enables parallel display or overlapping display of a normal image and a narrow-band light image.

As described above, each of the above-described embodiments and each of the modifications (including the modifications of each embodiment) enable provision of an endoscope apparatus capable of clearly displaying blood vessels in a deep part of a mucous membrane with proper brightness without troublesome work such as medical agent administration.

The present invention is not limited to the above-described embodiments, alterations and the like are possible without departing from the spirit of the present invention.

What is claimed is:

1. An endoscope apparatus comprising:
   an illumination section that irradiates at least one illuminating light having a predetermined wavelength band to a subject;
   an image pickup section that picks up an image of return light from the subject based on the irradiation by the illumination section;
   an image signal processing section that generates an image signal based on an image pickup signal from the image pickup section;
   a light-adjusting section that, based on a first luminance value based on a signal with a first wavelength band that is a narrow band and a second luminance value based on a signal with a second wavelength band that is a narrow band between a wavelength band providing a maximal value and a wavelength band providing a minimal value in a light absorption characteristic of hemoglobin in a body tissue of the subject in a red band in a visible range, the second wavelength band being within the red band in the visible range, providing an absorption coefficient lower than that of the signal of the first wavelength band in the light absorption characteristic of hemoglobin and providing a suppressed scattering characteristic of the body tissue, and a third luminance value based on a signal with a third wavelength band that is a narrow band, the third wavelength band being a wavelength band outside the red band, and providing an absorption coefficient higher than that of the signal with the first wavelength band in the absorption characteristic, performs processing for addition by adding a weight coefficient larger than a weight coefficient to be added to the third luminance value to the first luminance value and the second luminance value to calculate a light adjustment reference signal for adjusting a light amount in the illumination section and outputs the light adjustment reference signal;
   and an illumination control section that controls an amount of light irradiated by the illumination section based on the light adjustment reference signal outputted from the light-adjusting section.

2. The endoscope apparatus according to claim 1, wherein the image signal processing section generates the image signal based on the signal with the first wavelength band, the signal with the second wavelength band, and the signal with the third wavelength band.

3. The endoscope apparatus according to claim 2, further comprising a color balance-adjusting section that amplifies a strength of the signal with the third wavelength band by a predetermined amount relative to a strength of the signal with the second wavelength band to perform color balance adjustment for in vivo information discrimination.

4. The endoscope apparatus according to claim 1,
   wherein the illumination section irradiates the at least one illuminating light via a band limiting section that limits the illuminating light to the first wavelength band and the second wavelength band; and
   wherein the image signal processing section generates the image signal based on an image pickup signal for the first wavelength band and an image pickup signal for the second wavelength band, the image pickup signals being obtained as a result of an image of the return light being picked up by the image pickup section.

5. The endoscope apparatus according to claim 1,
   wherein the image pickup section receives the return light via a band limiting section that limits the return light to the first wavelength band and the second wavelength band and picks up an image of the return light; and wherein the image signal processing section generates the image signal based on the image pickup signal with the first wavelength band and the image pickup signal with the second wavelength band obtained as a result of an image of the return light being picked up by the image pickup section.

6. The endoscope apparatus according to claim 1, wherein the image signal processing section generates the signal with the first wavelength band and the signal with the second wavelength band by performing spectral estimation processing on the image pickup signal of the return light and outputs the image signal.

7. The endoscope apparatus according to claim 1, wherein the image signal processing section generates an image signal from the signal with the first wavelength band by performing spectral estimation processing and outputs the image signal.

8. The endoscope apparatus according to claim 1, wherein the image signal processing section generates an image signal from the signal with the second wavelength band by performing spectral estimation processing and outputs the image signal.

9. The endoscope apparatus according to claim 1, wherein the first wavelength band includes a peak wavelength of the spectral characteristic in a range of from a wavelength of 585 nm to a wavelength of 615 nm.

10. The endoscope apparatus according to claim 1, wherein the second wavelength band includes a peak wavelength of the spectral characteristic in a range of from a wavelength of 610 nm to a wavelength of 730 nm.

11. The endoscope apparatus according to claim 1, wherein the second wavelength band includes a wavelength peak or a center wavelength of the spectral characteristic in a range of wavelength of 730 nm or more.

12. The endoscope apparatus according to claim 1, wherein the third wavelength band includes a peak wavelength of the spectral characteristic in a range of from a wavelength of 400 nm to a wavelength of no more than 585.

13. The endoscope apparatus according to claim 1,
wherein the endoscope apparatus has a normal light observation mode and a narrow-band light observation mode; and
wherein the light-adjusting section calculates and outputs the light adjustment reference signal in the narrow-band light observation mode.

14. The endoscope apparatus according to claim 1, wherein the weight coefficient to be added to the first luminance value is larger than the weight coefficient to be added to the second luminance value in the processing for addition in the light-adjusting section.

15. The endoscope apparatus according to claim 14, wherein magnitudes of the weight coefficients in calculating the light adjustment reference signal are set in order of the first luminance value, the second luminance value, and the third luminance value.

* * * * *